US010744197B2

(12) United States Patent
Shishido et al.

(10) Patent No.: US 10,744,197 B2
(45) Date of Patent: Aug. 18, 2020

(54) VACCINE PHARMACEUTICAL COMPOSITION FOR ORAL ADMINISTRATION AND METHOD FOR MANUFACTURING VACCINE PHARMACEUTICAL COMPOSITION FOR ORAL ADMINISTRATION

(71) Applicant: NITTO DENKO CORPORATION, Osaka (JP)

(72) Inventors: Takuya Shishido, Osaka (JP); Daisuke Asari, Osaka (JP); Eiji Kiyotoh, Osaka (JP); Kyohei Matsushita, Osaka (JP); Wenjing Li, Osaka (JP); Masahiro Fukasaka, Osaka (JP); Katsuyuki Okubo, Osaka (JP); Mitsuhiko Hori, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 15/777,396

(22) PCT Filed: Nov. 28, 2016

(86) PCT No.: PCT/JP2016/085155
§ 371 (c)(1),
(2) Date: May 18, 2018

(87) PCT Pub. No.: WO2017/090766
PCT Pub. Date: Jun. 1, 2017

(65) Prior Publication Data

US 2018/0326041 A1 Nov. 15, 2018

(30) Foreign Application Priority Data

Nov. 27, 2015 (JP) ................................ 2015-232453

(51) Int. Cl.

| | |
|---|---|
| ***A61K 39/00*** | (2006.01) |
| ***C07K 14/00*** | (2006.01) |
| ***C12N 9/90*** | (2006.01) |
| ***A61K 38/00*** | (2006.01) |
| ***A61K 39/108*** | (2006.01) |
| ***A61K 39/145*** | (2006.01) |
| ***A61K 47/26*** | (2006.01) |
| ***A61K 47/36*** | (2006.01) |
| ***A61K 47/38*** | (2006.01) |
| ***A61K 9/19*** | (2006.01) |
| ***A61P 31/16*** | (2006.01) |
| ***A61K 47/18*** | (2017.01) |

(52) U.S. Cl.
CPC .............. *A61K 39/145* (2013.01); *A61K 9/19* (2013.01); *A61K 47/183* (2013.01); *A61K 47/26* (2013.01); *A61K 47/36* (2013.01); *A61K 47/38* (2013.01); *A61P 31/16* (2018.01); *A61K 2039/5252* (2013.01); *A61K 2039/542* (2013.01); *A61K 2039/55511* (2013.01); *A61K 2039/70* (2013.01)

(58) Field of Classification Search
CPC ................ A61K 2300/00; A61K 39/00; A61K 2039/505; A61K 31/56; C12N 15/8245
See application file for complete search history.

(56) References Cited

U.S. PATENT DOCUMENTS

| | | | | |
|---|---|---|---|---|
| 2003/0219475 A1* | 11/2003 | Truong-Le ........... | A61K 9/0019 424/450 |
| 2004/0013695 A1* | 1/2004 | Vande-Velde ........ | A61K 9/0053 424/400 |
| 2010/0104595 A1 | 4/2010 | Yamashita | |
| 2016/0220483 A1* | 8/2016 | Mistilis ................ | A61K 9/0021 |

FOREIGN PATENT DOCUMENTS

| | | | |
|---|---|---|---|
| CN | 101524537 | A | 9/2009 |
| EP | 3 381 468 | A1 | 10/2018 |
| JP | 2004-506020 | A | 2/2004 |
| JP | 2005-538939 | A | 12/2005 |
| JP | 5388842 | B2 | 10/2013 |
| WO | 02/13858 | A1 | 2/2002 |
| WO | 02/101412 | A2 | 12/2002 |
| WO | 03/087327 | A2 | 10/2003 |
| WO | 2004/058156 | A2 | 7/2004 |
| WO | WO 2007/038926 | A1 | 4/2007 |
| WO | WO2012158978 | * | 11/2012 |

OTHER PUBLICATIONS

International Search Report from Patent Application No. PCT/JP2016/085155, dated Jan. 17, 2017.
International Preliminary Report on Patentability from Patent Application No. PCT/JP2016/085155, dated May 29, 2018.
EESR for EP App. No. 16 86 8709.3 dated May 6, 2019.

* cited by examiner

*Primary Examiner* — Barry A Chestnut
(74) *Attorney, Agent, or Firm* — Greenblum & Bersntein, P.L.C.

(57) ABSTRACT

The present invention provides a vaccine pharmaceutical composition for oral administration that enables stable storage of an influenza virus antigen and a method for producing the pharmaceutical composition. Provided is a vaccine pharmaceutical composition for oral administration containing an influenza virus antigen, an excipient, a disaccharide, and an amino acid.

16 Claims, 2 Drawing Sheets

VACCINE PHARMACEUTICAL COMPOSITION FOR ORAL ADMINISTRATION AND METHOD FOR MANUFACTURING VACCINE PHARMACEUTICAL COMPOSITION FOR ORAL ADMINISTRATION

TECHNICAL FIELD

The present invention relates to a vaccine pharmaceutical composition for oral administration containing an influenza virus antigen. The present invention particularly relates to a vaccine pharmaceutical composition for oral administration having excellent stability of an influenza virus antigen and excellent convenience in terms of storage, handleability, and the like. The present invention also relates to a method for producing the same.

BACKGROUND ART

Influenza is a type of acute infection caused by an influenza virus. The incubation period from infection with the influenza virus to onset of influenza is usually one to two days. The onset is accompanied by the following symptoms, for example: a fever of 38 degrees or higher, systemic symptoms (such as general malaise, headache, joint pain, and muscle pain), sore throat, cough, and nasal discharge. In general, recovery takes one week or less. Influenza may lead to complications such as pneumonia and bronchitis, which may become severe and result in death, in the case of onset of influenza in people such as elderly people, infants, pregnant women, patients with chronic respiratory disease, patients with chronic cardiovascular disease, diabetic patients, and chronic renal failure patients. In addition, influenza intensively occurs in epidemics in a short period of time, and thus sometimes affects the society and causes an economic loss.

Administration of influenza vaccine is the most effective method of preventing influenza from becoming severe. An influenza vaccine preparation is usually a liquid preparation used as an injectable drug or nasal preparation.

For distribution of a liquid preparation of influenza vaccine, a low temperature must be maintained throughout the entire process of distribution and storage (so-called a cold chain) in order to prevent deactivation of an influenza vaccine. Although the epidemic season is different depending on the region, influenza is pandemic, and it is difficult to distribute the preparation while maintaining the activity of the influenza vaccine antigen in the countries and regions where it is difficult to maintain a low temperature.

Currently available influenza vaccines are roughly divided into live attenuated influenza vaccines and inactivated influenza vaccines. Further, inactivated influenza vaccines are classified into the following three groups: (1) whole virus inactivated with formalin or the like; (2) split vaccine obtained by disrupting virus particles with an organic solvent or a surfactant and solubilizing lipid envelopes; and (3) subunit vaccine obtained by purifying hemagglutinin (HA) and neuraminidase (NA). Among these, two types of vaccines, i.e., split vaccines and subunit vaccines, are currently available as commercial influenza vaccines. Both of these vaccines are usually prepared by disrupting virus particles with an organic solvent or a surfactant and isolating or purifying viral proteins depending on the type.

However, while influenza virus particles have a high sterol content and are usually stable, problems such as a time-dependent decrease in the titer occur during a storage period in the case where the vaccine is obtained by disrupting virus particles, removing lipid substances from the virus particles, and isolating or purifying viral proteins. As described above, since the split vaccine and the subunit vaccine are not necessarily stable, a low temperature must be maintained throughout the entire process of distribution and storage in order to maintain the activity of the influenza virus antigen.

As a method of overcoming the above-described drawback of the liquid preparation of influenza vaccine, an attempt has been made to produce a preparation in dry form.

Patent Literature 1 discloses production of particles by spray-drying an influenza virus together with a thickener. Patent Literature 2 discloses production of a powder by spray-drying an antigen together with various additives. Patent Literature 3 discloses a pharmaceutical composition in which the activity of an attenuated influenza virus as a live influenza vaccine is stabilized by lyophilizing a vaccine solution containing sucrose as a stabilizer, dextran as a bonding agent, and xanthan gum as an excipient.

Patent Literature 4 discloses a pharmaceutical composition in which the activity of an influenza HA vaccine is stabilized by lyophilizing a vaccine solution containing a hydrophobic amino acid (phenylalanine, valine, leucine, and isoleucine) and arginine hydrochloride as stabilizers.

A seasonal influenza vaccine is a vaccine reformulated annually for specific strains, and a mixed type vaccine containing a trivalent influenza virus antigen (two strains of type A and one strain of type B) or a tetravalent influenza virus antigen (two strains of type A and two strains of type B) is a mainstream vaccine. However, since the amino acid sequence or conformation is different according to the viral type, it is difficult to stably store a pharmaceutical composition containing plural influenza virus antigens by conventional vaccine formulation techniques.

CITATION LIST

Patent Literature

Patent Literature 1: WO 2004/058156
Patent Literature 2: WO 2002/101412
Patent Literature 3: WO 2002/013858
Patent Literature 4: JP 5388842 B

SUMMARY OF INVENTION

Technical Problem

The present invention aims to provide a vaccine pharmaceutical composition for oral administration which enables stable storage of an influenza virus antigen and a method for producing the pharmaceutical composition.

Solution to Problem

The present inventors made intensive studies to solve the above problem to find that combination of a specific excipient, a specific disaccharide, and a specific amino acid enables stable storage of an influenza virus antigen in a pharmaceutical composition. Thus, the present invention was completed.

The phrase "stable storage" as used herein means that the activity of an influenza virus antigen contained in a dried preparation is not lowered during the production process of the dried preparation to allow the influenza virus antigen to exhibit high activity and the activity of the influenza virus antigen can be stably maintained even if the dried preparation is stored without strictly maintaining a low temperature.

Specifically, the present invention relates to a vaccine pharmaceutical composition for oral administration including an influenza virus antigen, an excipient, a disaccharide, and an amino acid.

The excipient is preferably at least one selected from the group consisting of dextran, hydroxypropyl cellulose, and hydroxypropyl methylcellulose. The disaccharide is at least one selected from the group consisting of trehalose, isomalt, sucrose, maltose, melibiose, palatinose, and lactulose.

The amino acid is preferably at least one selected from the group consisting of arginine, lysine, proline, threonine, ornithine, glycine, and salts of these.

The vaccine pharmaceutical composition for oral administration is preferably a dried preparation, and the dried preparation is preferably a tablet.

The excipient preferably contains dextran. The amount of the dextran is preferably 30 to 95% by mass relative to the mass of the solid content of the vaccine pharmaceutical composition for oral administration.

The amino acid preferably contains at least one selected from the group consisting of arginine and a salt thereof. The amount of the at least one selected from the group consisting of arginine and a salt thereof is preferably 1 to 19% by mass relative to the mass of the solid content of the vaccine pharmaceutical composition for oral administration.

The salt of an amino acid is preferably an inorganic salt. The inorganic salt is preferably hydrochloride.

In the vaccine composition for oral administration of the present invention, the influenza virus antigen is preferably an inactivated antigen. The inactivated antigen is preferably a split vaccine antigen or a subunit vaccine antigen.

The influenza virus antigen is preferably a multivalent antigen containing plural antigens.

The present invention also relates to a method for producing a vaccine pharmaceutical composition for oral administration, including the steps of: preparing a vaccine-containing preparation solution that contains an influenza virus antigen, an excipient, a disaccharide, an amino acid, and a solvent; and drying the vaccine-containing preparation solution.

The present invention also relates to a method for producing a vaccine pharmaceutical composition for oral administration, including the steps of: preparing a vaccine-containing preparation solution that contains an influenza virus antigen, an excipient, a disaccharide, an amino acid, and a solvent; and drying the vaccine-containing preparation solution, wherein the vaccine-containing preparation solution is dried by lyophilization, and the vaccine-containing preparation solution contains 5% by mass or more of the excipient relative to the mass of the vaccine-containing preparation solution and 30% by mass or more of the excipient relative to the mass of the solid content of the vaccine-containing preparation solution.

The present invention is specifically described in the following.

The vaccine pharmaceutical composition for oral administration of the present invention contains an influenza virus antigen.

In the vaccine pharmaceutical composition for oral administration of the present invention, the strain of the influenza virus used in the influenza virus antigen is not particularly limited. Examples include an influenza A virus strain and an influenza B virus strain. The influenza virus antigen preferably contains two or more types of influenza virus antigens including one or more influenza A antigens and one or more influenza B antigens. In particular, the influenza virus antigen preferably contains at least one influenza virus antigen selected from A(H1N1), A(H3N2), B/Yamagata lineage, B/Victoria lineage, and B/Brisbane lineage.

The influenza virus antigen is not particularly limited, and may contain a live virus or an inactivated antigen. In particular, the influenza virus antigen is preferably an inactivated antigen. The inactivated antigen may be an inactivated whole virus, a split vaccine antigen, or a subunit vaccine antigen, preferably a split vaccine antigen or a subunit vaccine antigen, more preferably a split vaccine antigen.

The split vaccine antigen or subunit vaccine antigen may be prepared by any method. For example, it may be prepared in the following manner: growing virus particles in embryonated eggs; disrupting the virus particles with an organic solvent or a surfactant; and isolating or purifying viral proteins depending on the type.

The type of the split vaccine antigen is not particularly limited. Examples include hemagglutinin (HA) antigen, neuraminidase (NA) antigen, matrix (M1) antigen, matrix (M2) antigen, and nucleoprotein (NP) antigen. Among these, preferred is hemagglutinin (HA) antigen that is a virus surface antigen, in view of inducing immunity that is effective for viral infection control by administration of the vaccine pharmaceutical composition for oral administration.

In the vaccine composition for oral administration of the present invention, the influenza virus antigen is preferably a multivalent antigen containing plural antigens. The multivalent antigen can work on a greater variety of influenza viruses.

A method for producing the influenza virus antigen is not particularly limited, and any conventionally known method may be employed. For example, the influenza virus antigen can be produced from a virus stock solution that is prepared by infecting chicken eggs, cells, or the like with influenza virus strains isolated from patients with influenza or animals infected with influenza and culturing the virus strains, followed by purification. Alternatively, the influenza virus antigen can be produced from a genetically engineered recombinant virus or specific antigen produced in various cells.

In the vaccine pharmaceutical composition for oral administration of the present invention, the amount of the influenza virus antigen is only required to be at least an effective amount. For example, in the vaccine pharmaceutical composition for oral administration of the present invention, the total amount (mass) of HA antigen(s) serving as active ingredient(s) is preferably within a range of 0.01 μg to 1.0 mg per dose. If the amount is less than 0.01 μg, the infection control or the function as a therapeutic agent may be insufficient. If the amount is more than 1.0 mg, a safety problem may arise. The lower limit of the amount of the antigen is more preferably 0.1 μg and the upper limit thereof is more preferably 500 μg.

The "mass of the antigen" as used herein refers to the total mass of the HA antigen proteins contained in the antigen in the vaccine pharmaceutical composition, unless otherwise specified. Accordingly, in the case where the antigen is a substance derived from a living body such as viruses, the mass of the antigen refers to the mass of HA antigen protein(s) contained in the antigen. In the case where plural antigens are contained, the total mass thereof is meant.

The vaccine pharmaceutical composition for oral administration of the present invention contains an excipient, a disaccharide, and an amino acid.

The vaccine pharmaceutical composition for oral administration of the present invention containing these components can stably maintain the activity of the influenza virus antigen even if the composition is stored without strict temperature/humidity control.

The excipient is preferably at least one selected from the group consisting of dextran, hydroxypropyl cellulose, and hydroxypropyl methylcellulose.

The excipient stabilizes the activity of the influenza virus antigen. The excipient is more preferably dextran because it has excellent excipient effect and an effect of stabilizing the activity of the influenza virus antigen.

The amount, as the total amount, of the excipient(s) is preferably 1 to 30% by mass, more preferably 2 to 20% by mass, still more preferably 5 to 20% by mass relative to the total mass of the vaccine-containing preparation solution that contains an influenza virus antigen, an excipient, a disaccharide, an amino acid, and a solvent.

If the total amount of the excipient(s) is less than 1% by mass, the pharmaceutical composition may not be provided in an appropriate dosage form as a medicine after drying. If the total amount of the excipient(s) is more than 30% by mass, it may not be uniformly dispersed or dissolved in the preparation solution, possibly causing problems in the production. With the lower limit of the amount of the excipient (s) set to 5% by mass, the vaccine pharmaceutical composition for oral administration of the present invention can be suitably used in the form of a tablet.

The total amount of the excipient(s) is preferably 30 to 95% by mass, more preferably 40 to 85% by mass relative to the mass of the solid content of the vaccine pharmaceutical composition for oral administration. If the amount is less than 30% by mass, the pharmaceutical composition may not be provided in an appropriate dosage form.

In the case where the excipient is dextran, the amount of the dextran is preferably 30 to 95% by mass relative to the mass of the solid content of the vaccine pharmaceutical composition for oral administration. If the amount is less than 30% by mass, an inconvenience may occur upon use of the pharmaceutical composition in a tablet form. If the amount is more than 95% by mass, the stabilizer content is relatively lowered, possibly leading to insufficient vaccine stability.

The disaccharide is preferably at least one selected from the group consisting of trehalose, isomalt, sucrose, maltose, melibiose, palatinose, and lactulose.

The disaccharide is more preferably at least one selected from the group consisting of trehalose, isomalt, and sucrose. Any of these disaccharides stabilizes the activity of the influenza virus antigen and is well dissolved in a solvent, and therefore is easily added to the vaccine-containing preparation solution that contains an influenza virus antigen, an excipient, a disaccharide, an amino acid, and a solvent.

The disaccharide is still more preferably at least one selected from the group consisting of trehalose and isomalt in terms of hygroscopicity.

The disaccharide is particularly preferably trehalose.

The total amount of the disaccharide(s) is preferably 0.1 to 20% by mass, more preferably 0.5 to 10% by mass relative to the total mass of the vaccine-containing preparation solution that contains an influenza virus antigen, an excipient, a disaccharide, an amino acid, and a solvent.

If the total amount of the disaccharide(s) is less than 0.1% by mass, the vaccine stability after drying may be insufficient. If the total amount of the disaccharide(s) is more than 20% by mass, the viscosity of the preparation solution becomes very high, possibly causing problems in the production. In addition, the hygroscopicity of the pharmaceutical composition increases to lower the activity of the influenza antigen if the pharmaceutical composition is stored without strict humidity control.

The total amount of the disaccharide(s) is preferably 10 to 70% by mass, more preferably 12 to 68% by mass relative to the mass of the solid content of the vaccine pharmaceutical composition for oral administration.

If the total amount of the disaccharide(s) is less than 10% by mass, the vaccine stability may be insufficient. If the total amount of the disaccharide(s) is more than 70% by mass, inconvenience may occur in terms of the moldability of a tablet and upon use.

The amino acid is preferably at least one selected from the group consisting of arginine, lysine, proline, threonine, ornithine, glycine, and salts of these. Any of these amino acids stabilizes the activity of the influenza virus antigen and is well dissolved in a solvent, and therefore is easily added to the vaccine-containing preparation solution that contains an influenza virus antigen, an excipient, a disaccharide, an amino acid, and a solvent.

The amino acid is more preferably an L-amino acid.

The amino acid is more preferably at least one selected from the group consisting of arginine, lysine, proline, threonine, ornithine, and salts of these because they are less likely to cause yellowing.

The amino acid is still more preferably at least one selected from the group consisting of arginine, a salt of arginine, lysine hydrochloride, proline, threonine, and ornithine hydrochloride. The reason for this is that because the activity of an influenza virus antigen contained in the dried preparation is not lowered during the production process of the dried preparation to allow the influenza virus antigen to exhibit high activity and that the activity of the influenza virus antigen can be stably maintained even if the dried preparation is stored without strict humidity control.

The amino acid is particularly preferably at least one selected from the group consisting of arginine, a salt of arginine, proline, threonine, and lysine hydrochloride.

The amino acid is further more preferably at least one selected from the group consisting of arginine, a salt of arginine, and lysine hydrochloride, most preferably at least one selected from the group consisting of arginine and a salt thereof. The use of arginine hydrochloride and/or lysine hydrochloride, in particular, the use of arginine hydrochloride more effectively stabilizes the activity of H1N1 antigen, and H3N2 antigen. As described above, the use of arginine hydrochloride as the amino acid can stably maintain various influenza virus antigens different in the stability.

The salt as used herein refers to any organic acid salt or inorganic acid salt. Preferred is a pharmaceutically acceptable inorganic salt. In particular, more preferred is hydrochloride.

The amount of the amino acid is preferably 0.01 to 4% by mass, more preferably 0.05 to 2% by mass relative to the total mass of the vaccine-containing preparation solution that contains an influenza virus antigen, an excipient, a disaccharide, an amino acid, and a solvent.

If the amount of the amino acid is less than 0.01% by mass, the vaccine stability after drying may be insufficient. If the amount of the amino acid is more than 4% by mass, the amino acid may not be uniformly dispersed or dissolved in the preparation solution, possibly leading to problems in the production. In addition, the hygroscopicity of the pharmaceutical composition may increase, so that the activity of the influenza virus antigen may be lowered if the composition is stored without humidity control.

The amount of the amino acid is preferably 1 to 19% by mass, more preferably 1.5 to 18.5% by mass relative to the mass of the solid content of the vaccine pharmaceutical composition for oral administration. If the amount of the amino acid is less than 1% by mass, the vaccine stability achieved may be insufficient. If the amount is more than 19% by mass, inconvenience may occur in terms of the moldability of a tablet and upon use.

In the case where the amino acid is at least one selected from the group consisting of arginine and a salt thereof, the amount thereof is preferably 1 to 19% by mass relative to the total mass of the vaccine pharmaceutical composition for oral administration. If the amount is less than 1% by mass, the vaccine stability after drying may be insufficient. If the amount of the at least one selected from the group consisting of arginine and a salt thereof is more than 19% by mass, it may not be uniformly dispersed or dissolved in the preparation solution, possibly leading to problems in the production. In addition, the hygroscopicity of the pharmaceutical composition may increase, so that the activity of the influenza virus antigen may be lowered if the composition is stored without humidity control.

The "amount" refers to the proportion of the amino acid, i.e., at least one selected from arginine and a salt thereof, in the solid content of the vaccine pharmaceutical composition for oral administration.

The vaccine pharmaceutical composition for oral administration of the present invention preferably contains an immunostimulant (adjuvant).

The adjuvant may be at least one selected from the group consisting of a toll-like receptor 4 (TLR4) agonist, a toll-like receptor 2/6 (TLR2/6) agonist, and a cyclic dinucleotide or a derivative or salt thereof. Preferred among these is a TLR4 agonist.

The TLR4 agonist is preferably a lipopolysaccharide or a salt thereof. The lipopolysaccharide as used herein may be, as well as the lipopolysaccharide itself, a derivative or a variant thereof as long as it keeps the properties of the lipopolysaccharide.

The lipopolysaccharide may be an extract from a gram negative bacterial cell wall or a variant thereof, and may also be a synthetic lipopolysaccharide.

Examples of the gram negative bacterium include bacteria of genus *Acetobacter*, genus *Achromobacter*, genus *Acidicaldus*, genus *Acidiphilium*, genus *Acidisphaera*, genus *Acidocella*, genus *Acidomonas*, genus *Agrobacterium*, genus *Asaia*, genus *Bacillus*, genus *Belnapia*, genus *Brucella*, genus *Bacteroides*, genus *Bordetella*, genus *Clostridium*, genus *Craurococcus*, genus *Chlamydia*, genus *Enterobacter*, genus *Escherichia*, genus *Flavobacterium*, genus *Francisella*, genus *Gluconacetobacter*, genus *Gluconobacter*, genus *Haemophilus*, genus *Kozakia*, genus *Klebsiella*, genus *Leahibacter*, genus *Leclercia*, genus *Legionella*, genus *Methanoculleus*, genus *Methanosarcina*, genus *Micrococcus*, genus *Muricoccus*, genus *Neisseria*, genus *Neoasaia*, genus *Oleomonas*, genus *Pantoea*, genus *Plesiomonas*, genus *Paracraurococcus*, genus *Pseudomonas*, genus *Prophyromonas*, genus *Proteus*, genus *Rahnella*, genus *Rhodopila*, genus *Roseococcus*, genus *Rubritepida*, genus *Salmonella*, genus *Shigella*, genus *Stenortophomonas*, genus *Saccharibacter*, genus *Serratia*, genus *Stella*, genus *Swaminathania*, genus *Vibrio*, genus *Vparahaemolyticus*, genus *Teichococcus*, genus *Xanthomonas*, genus *Yersinia*, genus *Zymomonas*, and genus *Zavarzinia*. Preferred examples of the gram negative bacteria include bacteria of genus *Eschericha*, genus *Shigella*, genus *Salmonella*, genus *Klebsiella*, genus *Proteus*, genus *Yersinia*, genus *Vibrio*, genus *Vparahaemolyticus*, genus *Haemophilus*, genus *Pseudomonas*, genus *Legionella*, genus *Bordetella*, genus *Brucella*, genus *Francisella*, genus *Bacteroides*, genus *Neisseria*, genus *Chlamydia*, genus *Plesiomonas*, genus *Prophyromonas*, genus *Pantoea*, genus *Agrobacterium*, genus *Stenortophomonas*, genus *Enterobacter*, genus *Acetobacter*, genus *Xanthomonas*, and genus *Zymomonas*.

In particular, an extract or variant obtained from bacteria of genus *Escherichia*, genus *Salmonella*, genus *Pantoea*, genus *Acetobacter*, genus *Zymomonas*, genus *Xanthomonas*, or genus *Enterobacter* is preferred. They are contained in many kinds of food and herbal medicines used from ancient times and therefore are guaranteed to be safe to living bodies. In particular, an extract or variant obtained from bacteria of genus *Pantoea* is now used as health food and is considered to be more effective. The extracts or variants derived from these bacteria can be used as they are.

In the case where the extract obtained from a gram negative bacterial cell wall or a purified lipopolysaccharide is used as the lipopolysaccharide, the safety thereof to living bodies commonly needs to be considered. Variants obtained by detoxifying these may also be used. In contrast, bacteria of genus *Acetobacter* (e.g., *Acetcbacter aceti, Acetobacter xylinum, Acetobacter orientalis*), genus *Zymomonas* (e.g., *Zymomonas mobilis*), genus *Xanthomonas* (e.g., *Xanthomonas campestris*), genus *Enterobacter* (e.g., *Enterobacter cloacae*), and genus *Pantoea* (e.g., *Pantoea agglomerans*) are contained in many kinds of food and herbal medicines used from ancient times and therefore are guaranteed to be safe to living bodies. Accordingly, extracts derived from these bacteria or a purified lipopolysaccharide can be used as they are.

Examples of the derivatives of lipopolysaccharide include derivatives obtained by removing the polysaccharide moiety of lipopolysaccharide, specifically, Lipid A, monophosphoryl lipid A, and 3-deacylated monophosphoryl lipid A (3D-MPL).

The Lipid A obtained by removing the polysaccharide moiety of lipopolysaccharide may be an isolate derived from the gram negative bacterium or one synthesized to have the same structure as that of the isolate derived from the gram negative bacterium.

As a variant of the Lipid A, a dephosphorylated monophosphoryl lipid or a salt or derivative thereof may also be suitably used. A derivative of a monophosphoryl lipid may be used in the present invention as long as it keeps properties as an adjuvant. In particular, from the standpoint of safety to living bodies, 3D-MPL having a record as an immunostimulant for medical applications or a non-deacylated synthetic glucopyranosyl lipid as disclosed in US 2010/0310602 A is preferred.

The monophosphoryl lipid may also be suitably one derived from *Salmonella* which is safe and has been used precedently.

The cyclic dinucleotide is preferably a cyclic dipurine nucleotide, and may also be a salt or derivative thereof as long as it keeps properties of a cyclic dipurine nucleotide. As the cyclic dipurine nucleotide, for example, c-di-GMP that is a cyclic diguanosine monophosphate or c-di-AMP that is a cyclic diadenosine monophosphate is preferably used in terms of the safety.

The amount of the adjuvant in the vaccine pharmaceutical composition for oral administration of the present invention is preferably within a range of 0.1 μg to 100 mg per dose for each individual. If the amount is less than 0.1 μg, the infection control or the effect as a therapeutic agent may be insufficient. If the amount is more than 100 mg, a safety problem may arise. The lower limit of the amount of the immunostimulant is more preferably 0.3 μg and the upper limit thereof is more preferably 50 mg.

The vaccine pharmaceutical composition for oral administration of the present invention may contain edible polymers combined as appropriate, in addition to the excipient, within a range that the effect of the present invention is not impaired.

The amount of the edible polymers is preferably 0.1 to 10% by mass based on the total mass of the vaccine pharmaceutical composition for oral administration of the present invention.

The pH of the vaccine-containing preparation aqueous solution is preferably 5.0 to 9.0 just before the drying in the production process of the vaccine pharmaceutical composition for oral administration of the present invention. With the pH within this range, a significant decrease in the physicochemical stability of the vaccine pharmaceutical composition for oral administration of the present invention can be prevented, and the safety can be favorably ensured. The pH of the vaccine-containing preparation aqueous solution is more preferably 6.0 to 8.0.

In order to favorably achieve the effect of the present invention, the vaccine pharmaceutical composition for oral administration of the present invention is preferably in the form of a dried preparation.

The dried preparation as used herein refers to a preparation having a moisture content of 15% by mass or less. If the moisture content is more than 15% by mass, deterioration in characteristics such as discoloration and deformation or reduction in the activity of the influenza virus antigen may occur when the preparation is stored without strictly maintaining a low temperature. Among the dried preparations, those having a moisture content of 10% by mass or less are particularly referred to as low-moisture-content dried preparations. In order to more favorably achieve the effect of the present invention, the vaccine pharmaceutical composition for oral administration of the present invention is preferably in the form of a low-moisture-content dried preparation.

The "moisture content" as used herein is determined in accordance with the Japanese Pharmacopoeia Sixteenth Edition, General test, Loss on Drying Test (hereafter, also simply referred to as a loss on drying test). In other words, the moisture content is determined from the mass reduction rate of a sample of the dried influenza vaccine preparation of the present invention after heating at 105° C. for three hours.

The vaccine pharmaceutical composition for oral administration of the present invention is useful as an influenza vaccine preparation because the influenza virus antigen contained in the dried preparation can exhibit its activity without a decrease in the activity even during the production process of the dried preparation, and is easily handleable compared to conventional liquid preparations.

Moreover, since the activity of the influenza virus antigen can be stably maintained even if the preparation is stored without strictly maintaining a low temperature, the preparation can be easily distributed and stored, compared to conventional liquid preparations.

The activity of the influenza virus antigen can be stably maintained even if the vaccine pharmaceutical composition for oral administration of the present invention is stored, for example, at 0° C. to 50° C. The lower limit of the storage temperature is more preferably 2° C. and the upper limit thereof is more preferably 40° C.

The vaccine pharmaceutical composition for oral administration of the present invention may be produced, for example, by drying a vaccine-containing solution that contains an influenza virus antigen, an excipient, a disaccharide, an amino acid, and a solvent. In this method, the activity of the influenza virus antigen in the vaccine pharmaceutical composition for oral administration of the present invention is not lowered in the drying process, and therefore, the influenza virus antigen can exhibit high activity.

The present invention also relates to a method for producing a vaccine pharmaceutical composition for oral administration, including the step of: preparing a vaccine-containing preparation solution that contains an influenza virus antigen, an excipient, a disaccharide, an amino acid, and a solvent; and drying the vaccine-containing preparation solution. The solvent is not particularly limited, and water or any organic solvent may be used. In terms of the safety, water is preferred.

The total amount of the influenza virus antigen(s) in the vaccine-containing preparation solution is, for example, 0.01 μgHA/mL or more. If the amount is less than 0.01 μgHA/mL, the effectiveness of the dried influenza vaccine preparation may be lowered. The lower limit of the amount is more preferably 0.1 μgHA/mL.

The upper limit of the amount of the influenza virus antigen in the vaccine-containing preparation solution is not particularly limited. In terms of the stability of the antigen, the amount of the influenza virus is preferably 500 μgHA/mL or less.

The influenza virus antigen may be dried by any method. Preferably, the influenza virus antigen is dried under non-thermal conditions because it is thermally unstable.

The method of drying under non-thermal conditions is not particularly limited. Yet, it is preferably a reduced-pressure drying method or a lyophilization method, with the lyophilization method being particularly preferred. The lyophilization method is not particularly limited. Any method that uses a conventionally known lyophilization device can be used.

The vaccine pharmaceutical composition for oral administration of the present invention may be used as a tablet, film, or particulate preparation obtained by drying the vaccine-containing preparation solution by lyophilization, or as a film preparation obtained by reduced-pressure drying the vaccine-containing preparation solution. Alternatively, it may be used as a tablet obtained by drying the vaccine-containing preparation solution, followed by mixing and tableting. Among these, a dried preparation obtained by lyophilization is preferred in terms of the stability. In particular, a tablet or film preparation is preferred because it is easily administered orally and has excellent handleability.

The present invention also encompasses a method including drying the vaccine-containing preparation solution by lyophilization.

In other words, the method for producing a vaccine pharmaceutical composition for oral administration of the present invention is a method for producing a vaccine pharmaceutical composition including the steps of: preparing a vaccine-containing preparation solution that contains an influenza virus antigen, an excipient, a disaccharide, an amino acid, and a solvent; and drying the vaccine-containing preparation solution, wherein the vaccine-containing preparation solution is dried by lyophilization, and the vaccine-containing preparation solution contains 5% by mass or more of the excipient relative to the mass of the vaccine-containing preparation solution and 30% by mass or more of the excipient relative to the mass of the solid content of the vaccine-containing preparation solution.

If the amount of the excipient relative to the mass of the vaccine-containing preparation solution is less than 5% by mass, the pharmaceutical composition may not be provided in an appropriate dosage form as a medicine after drying, and an inconvenience may occur upon use thereof as a tablet. If the amount of the excipient relative to the mass of the solid content is less than 30% by mass, an inconvenience may occur upon use of the pharmaceutical composition as a tablet.

The word "target" as used herein refers to a human or animal (e.g., mammal, bird).

The vaccine pharmaceutical composition for oral administration of the present invention exhibits a high effect of inducing humoral immunity in the target by oral administration of an influenza virus antigen.

The vaccine pharmaceutical composition for oral administration of the present invention may be administered to any part in the oral cavity, for example, under the tongue, on the tongue, back of the tongue, and buccal side. In particular, administration under the tongue is preferred.

The vaccine pharmaceutical composition for oral administration of the present invention may be stored in any container. Preferred is a hermetically sealable container. Examples thereof include aluminum packaging materials, blister packing, and vials for lyophilization.

In the vaccine pharmaceutical composition for oral administration of the present invention, the effect of inducing humoral immunity can be measured by an immunity induction test using a model animal for immunological evaluation and the ELISA method (antigen-specific IgG antibody and antigen-specific IgA antibody). Examples of a sample for measuring the humoral immunity by the ELISA method include a serum and a nasal cavity washing liquid of a model animal for immunological evaluation.

Advantageous Effects of Invention

The vaccine pharmaceutical composition for oral administration of the present invention can stably store an influenza virus antigen in the pharmaceutical composition. In a preferred embodiment, plural influenza virus antigens different in thermal stability can be stably stored in one pharmaceutical composition.

In other words, plural influenza virus antigens contained in the dried preparation can exhibit high activities without a decrease in their activities during the production of the dried preparation, and the activities of the plural influenza virus antigens different in thermal stability can be stably maintained even if the dried preparation is stored without strictly maintaining a low temperature.

The vaccine pharmaceutical composition for oral administration of the present invention can be used as it is or by being dissolved or dispersed in a solvent that can be administered to a living body (such as a normal saline solution or water for injection) upon use.

In addition, since the vaccine pharmaceutical composition for oral administration of the present invention has a high effect of inducing humoral immunity by oral administration of an influenza virus antigen to a target, the use thereof in a dosage form that allows oral administration contributes to excellent compliance based on the following factors. Specifically, noninvasive administration is allowed; patients are free from pain or fear of injections; patients can perform administration by themselves as the administration is easy; medical professionals can avoid a risk of infection due to needle pricking; in the case where repetitive administration is needed, the ambulatory frequency can be reduced to contribute to the improvement in quality of life of the patient; and medical wastes (e.g., needles) which necessitate special disposition are not generated. Moreover, administration of the vaccine pharmaceutical composition for oral administration of the present invention can induce higher mucosal immunity (IgA antibody) compared to injections.

DESCRIPTION OF EMBODIMENTS

Figure 1:
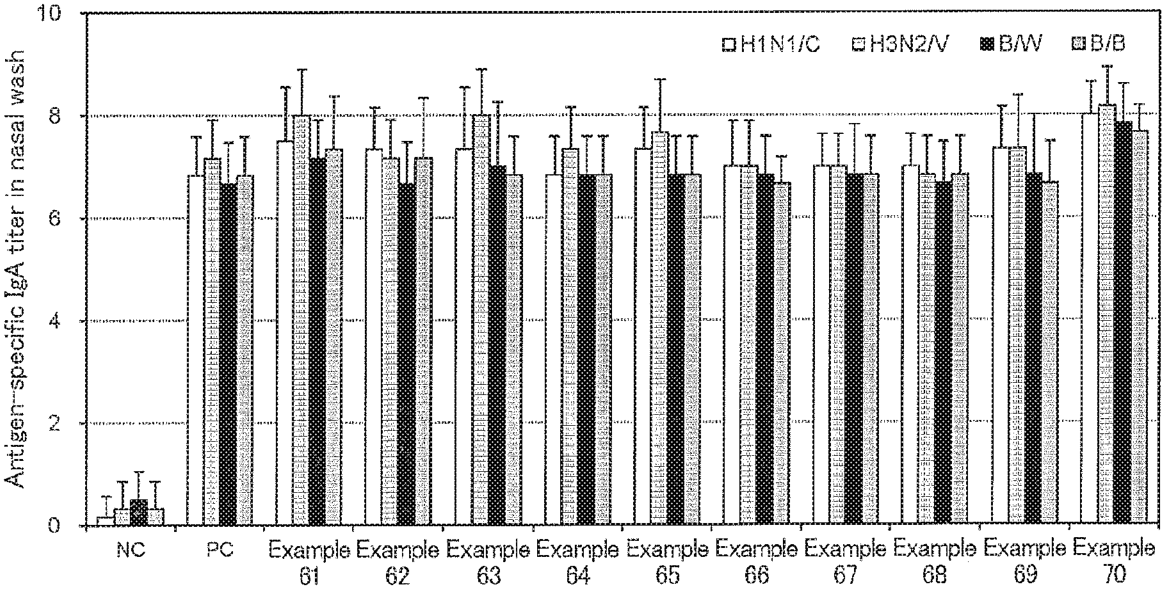
FIG. 1 is a graph showing the measurement results of the antigen-specific IgA titers of dried influenza vaccine preparations according to Examples 61 to 70 in mouse nasal cavity washing liquids.

The present invention is specifically described with reference to, but not limited to, examples. The unit "% by mass" as used herein refers to the mass percentage (mass/% by mass) of each material based on the total mass of the materials, unless otherwise specified.

A phosphate buffer for diluting a vaccine stock solution was prepared. Specifically, 3.53 g of dibasic sodium phosphate hydrate (Taihei Chemical Industrial Co., Ltd.), 0.54 g of sodium dihydrogen phosphate (Taihei Chemical Industrial Co., Ltd.), and 8.5 g of sodium chloride (Tomita Pharmaceutical Co., Ltd.) were dissolved in about 900 mL of purified water, and the solution was filled up to 1 L in a measuring flask.

Tetravalent mixed vaccine solutions were produced using season strains of influenza HA vaccines (all produced by Research Foundation for Microbial Diseases of Osaka University). Each HA vaccine stock solution was mixed and diluted with a phosphate buffer for vaccines to a final concentration of 120 μg/mL. The vaccine solution of 2012-2013 season strain is referred to as a tetravalent vaccine solution A and the vaccine solution of 2013-2014 season strain is referred to as a tetravalent vaccine solution B.

TABLE 1

| | Influenza HA vaccine | Abbreviation | HA concentration [ug/mL] |
|---|---|---|---|
| 2012/2013 season strain | A/California/7/2009(H1N1) | H1N1/C | 857 |
| | A/Victoria/361/2011(H3N2) | H3N2/V | 622 |
| | B/Wisconsin/60/2008 | B/W | 445 |
| | B/Brisbane/60/2008 | B/B | 579 |
| 2013/2014 season strain | A/California/7/2009(H1N1) | H1N1/C | 857 |
| | A/Texas/50/2012(H3N2) | H3N2/T | 688 |
| | B/Massachusetts/02/2012 | B/M | 488 |
| | B/Brisbane/60/2008 | B/B | 579 |

<Evaluation of Stabilization of the Activity of Influenza HA Antigen Given by Each Additive>

TEST EXAMPLE 1

As shown in Table 2, 5% by mass of dextran (dextran 70, available from Meito Sangyo Co., Ltd.) was added to 45% by mass of purified water, and appropriately stirred to be dissolved. An amount of 50% by mass of the tetravalent vaccine solution A was added thereto, mixed well and dissolved at room temperature. The obtained preparation solution was dispensed in 0.25-g portions in vials for lyophilization, and lyophilized to prepare a dried influenza vaccine preparation. The activity of the obtained dried influenza vaccine preparation immediately after the production was measured by the following method.

As a storage stability test, the obtained dried influenza vaccine preparation was stored at 40° C.±2° C. for two months, and the activity of each influenza HA antigen was measured by the following method. Table 4 shows the results.

<Single Radial Immunodiffusion Method (SRID Method)>

Agarose (AMRESCO) was added to the phosphate buffer to a concentration of 1% by mass, and heated to be completely dissolved. After a temperature decrease to about 60° C., an appropriate amount of an antiserum corresponding to the influenza HA antigen was added and stirred. The mixture was poured into a heat resistant vessel (10 cm in diameter), and cooled at room temperature to be solidified. Using a dedicated punch, 4×4 pieces of holes (4 mm in diameter) were made in the obtained solid, thereby preparing a gel for SRID analysis.

Each of the dried influenza vaccine preparations according to the test examples, comparative test examples, examples, and comparative examples was dissolved in the phosphate buffer and then diluted to a desired concentration. A surfactant (available from CALBIOCHEM, product name: ZWITTERGENT 3-14 Detergent) was further added to a final concentration of 1% and completely dissolved therein. Thus obtained solution was used as a sample solution.

As the standard solution, a 30 μg/mL solution of the influenza HA antigen was prepared using an influenza vaccine stock solution. At that time, additives contained in the sample solution (compounding agents and surfactants used in the preparation) were each added to the vaccine stock solution to the same final concentration as that of the sample solution, and appropriately diluted with the phosphate buffer to be completely dissolved. Similarly, a 22.5 μg/mL solution, a 15 μg/mL solution, and a 7.5 μg/mL solution of the influenza HA antigen were prepared.

The standard solutions at four concentrations and the sample solution were each applied to the SRID gel in an amount of 10 μL/well, and allowed to react under the wet condition at 25° C. for 18 to 24 hours.

The SRID gel taken out from the vessel was sandwiched between two sheets of filter paper, then further sandwiched between two sheets of paper having high absorbability, and dehydrated under a weight. The dehydrated gel was further subjected to air drying to be completely dried. The resulting gel was dyed in a coomassie brilliant blue (BIO-RAD) staining solution for an appropriate time, transferred to a destaining solution, and destained until an appropriate chromatic figure was obtained. Then, the SRID gel was spread on a GelBond Film (LONZA) and completely dried. The area of the obtained precipitate ring was measured using Image J software.

A calibration curve was created based on the concentrations and the areas of the obtained precipitate rings of the standard solutions. The area of the precipitate ring of the sample solution was measured, and the influenza HA antigen amount was calculated based on the calibration curve. The percentage of the obtained influenza HA antigen amount relative to the theoretical influenza HA antigen amount calculated from the amount shown in the table was calculated, and the obtained percentage was scored based on the following criteria.

5: 90% or higher but lower than 105%
4: 75% or higher but lower than 90%
3: 60% or higher but lower than 75%
2: 45% or higher but lower than 60%
1: 30% or higher but lower than 45%
0: Lower than 30%

(Characteristic Evaluation Method)

The obtained dried influenza vaccine preparations were evaluated based on the following criteria. After evaluation of the characteristics immediately after preparation, the characteristics were again evaluated after storage at 40° C.±2° C. in the same manner as in the stability evaluation.

Good: There is no inconvenience upon use.
Poor: There is inconvenience upon use.

TEST EXAMPLES 2 to 8, COMPARATIVE TEST EXAMPLES 1 to 8

Solutions were prepared in accordance with the formulations shown in Tables 2 and 3 in the same manner as in Test Example 1, and lyophilized to prepare dried influenza vaccine preparations. In Test Example 2, trehalose (trehalose G available from Asahi Kasei Chemicals Corporation) was used. In Test Example 3, isomalt (galen801 available from Beneo-Palatinit GmbH) was used. In Test Example 4, sucrose (Wako Pure Chemical Industries, Ltd.) was used. In Test Example 5, arginine hydrochloride (Kyowa Hakko Bio Co., Ltd.) was used. In Test Example 6, proline (Kyowa Hakko Bio Co., Ltd.) was used. In Test Example 7, threonine (Kyowa Hakko Bio Co., Ltd.) was used. In Test Example 8, lysine hydrochloride (Kyowa Hakko Bio Co., Ltd.) was used. In Comparative Test Example 2, glucose (Wako Pure Chemical Industries, Ltd.) was used. In Comparative Test Example 3, galactose (Wako Pure Chemical Industries, Ltd.) was used. In Comparative Test Example 4, fructose (Wako Pure Chemical Industries, Ltd.) was used. In Comparative Test Example 5, alanine (Wako Pure Chemical Industries, Ltd.) was used. In Comparative Test Example 6, valine (Wako Pure Chemical Industries, Ltd.) was used. In Comparative Test Example 7, isoleucine (Wako Pure Chemical Industries, Ltd.) was used. In Comparative Test Example 8, leucine (Wako Pure Chemical Industries, Ltd.) was used. As a storage stability test of the obtained dried influenza vaccine preparations, they were stored at 40° C.±2° C. for two months, and the activity of each influenza HA antigen was measured by the SRID method. The dried influenza vaccine preparations were evaluated in accordance with the characteristic evaluation method. The results were scored, and Table 4 shows the scores.

TEST EXAMPLE 9

An amount of 5% by mass of dextran was added to 45% by mass of purified water, and appropriately stirred to be dissolved. An amount of 50% by mass of the tetravalent vaccine solution B was added thereto, and mixed well. The obtained preparation solution was dispensed in 0.25-g portions in vials for lyophilization, and lyophilized to prepare a dried influenza vaccine preparation. As a storage stability test of the obtained dried influenza vaccine preparation, the activity of each influenza HA antigen was measured by the SRID method after storage at 40° C.±2° C. for two months. The dried influenza vaccine preparation was evaluated in accordance with the characteristic evaluation method. The results were scored, and Table 5 shows the scores.

TEST EXAMPLES 10 to 16, COMPARATIVE TEST EXAMPLES 9 to 16

Solutions were prepared in accordance with the formulations shown in Table 2 and 3 in the same manner as in Test Example 1, and lyophilized to prepare dried influenza vaccine preparations. As a storage stability test of the obtained dried influenza vaccine preparations, they were stored at 40° C.±2° C. for two months, and the activity of each influenza HA antigen was measured by the SRID method. The dried influenza vaccine preparations were evaluated in accordance with the characteristic evaluation method. The results were scored, and Table 5 shows the scores.

TABLE 2

| | Formulation [% by mass] Test Example | | | | | | | | | | | | | | | |
|---|---|---|---|---|---|---|---|---|---|---|---|---|---|---|---|---|
| Component | 1 | 2 | 3 | 4 | 5 | 6 | 7 | 8 | 9 | 10 | 11 | 12 | 13 | 14 | 15 | 16 |
| Tetravalent vaccine solution A | 50 | 50 | 50 | 50 | 50 | 50 | 50 | 50 | — | — | — | — | — | — | — | — |
| Tetravalent vaccine solution B | — | — | — | — | — | — | — | — | 50 | 50 | 50 | 50 | 50 | 50 | 50 | 50 |
| Dextran | 5 | — | — | — | — | — | — | — | 5 | — | — | — | — | — | — | — |
| Trehalose | — | 5 | — | — | — | — | — | — | — | 5 | — | — | — | — | — | — |
| Isomalt | — | — | 5 | — | — | — | — | — | — | — | 5 | — | — | — | — | — |
| Sucrose | — | — | — | 5 | — | — | — | — | — | — | — | 5 | — | — | — | — |
| Arginine hydrochloride | — | — | — | — | 5 | — | — | — | — | — | — | — | 5 | — | — | — |
| Proline | — | — | — | — | — | 5 | — | — | — | — | — | — | — | 5 | — | — |
| Threonine | — | — | — | — | — | | 5 | — | — | — | — | — | — | | 5 | — |
| Lysine hydrochloride | — | — | — | — | — | — | — | 5 | — | — | — | — | — | — | — | 5 |
| Purified water | 45 | 45 | 45 | 45 | 45 | 45 | 45 | 45 | 45 | 45 | 45 | 45 | 45 | 45 | 45 | 45 |

TABLE 3

| | Formulation [% by mass] Comparative Test Example | | | | | | | | | | | | | | | |
|---|---|---|---|---|---|---|---|---|---|---|---|---|---|---|---|---|
| Component | 1 | 2 | 3 | 4 | 5 | 6 | 7 | 8 | 9 | 10 | 11 | 12 | 13 | 14 | 15 | 16 |
| Tetravalent vaccine solution A | 50 | 50 | 50 | 50 | 50 | 50 | 50 | 50 | — | — | — | | — | — | — | — |
| Tetravalent vaccine solution B | — | — | — | — | — | — | — | — | 50 | 50 | 50 | 50 | 50 | 50 | 50 | 50 |
| Glucose | — | 5 | — | — | — | — | — | — | — | 5 | — | — | — | — | — | — |
| Galactose | — | — | 5 | — | — | — | — | — | — | — | 5 | — | — | — | — | — |
| Fructose | — | — | — | 5 | — | — | — | — | — | — | — | 5 | — | — | — | — |
| Alanine | — | — | — | — | 5 | — | — | — | — | — | — | — | 5 | — | — | — |
| Valine | — | — | — | — | — | 5 | — | — | — | — | — | — | — | 5 | — | — |
| Isoleucine | — | — | — | — | — | | 5 | — | — | — | — | — | — | | 5 | — |
| Leusine | — | — | — | — | — | — | — | 5 | — | — | — | — | — | — | — | 5 |
| Purified water | 50 | 45 | 45 | 45 | 45 | 45 | 45 | 45 | 50 | 45 | 45 | 45 | 45 | 45 | 45 | 45 |

TABLE 4

| | Activity of Influenza HA antigen | | | | | | | | |
|---|---|---|---|---|---|---|---|---|---|
| | H1N1/C | | H3N2/V | | B/W | | B/B | | |
| Antigen: [2012-13 strain] | Immediately after preparation | Two months later | Immediately after preparation | Two months later | Immediately after preparation | Two months later | Immediately after preparation | Two months later | Characteristics Two months later |
| Test Example 1 | 5 | 3 | 5 | 3 | 5 | 2 | 5 | 4 | Good |
| Test Example 2 | 5 | 4 | 4 | 1 | 5 | 4 | 5 | 4 | Poor |
| Test Example 3 | 5 | 4 | 4 | 1 | 5 | 4 | 5 | 4 | Poor |
| Test Example 4 | 5 | 4 | 4 | 0 | 5 | 4 | 5 | 4 | Poor |
| Test Example 5 | 5 | 4 | 5 | 4 | 3 | 3 | 3 | 1 | Poor |
| Test Example 6 | 5 | 3 | 5 | 4 | 2 | 2 | 4 | 1 | Poor |
| Test Example 7 | 4 | 3 | 5 | 4 | 5 | 2 | 5 | 3 | Poor |
| Test Example 8 | 5 | 4 | 5 | 4 | 4 | 3 | 5 | 2 | Poor |
| Comparative Test Example 1 | 2 | 0 | 2 | 0 | 2 | 0 | 2 | 0 | Poor |
| Comparative Test Example 2 | 5 | 0 | 5 | 0 | 4 | 0 | 4 | 0 | Poor |
| Comparative Test Example 3 | 5 | 0 | 4 | 0 | 4 | 0 | 4 | 0 | Poor |
| Comparative Test Example 4 | 5 | 0 | 4 | 0 | 4 | 0 | 4 | 0 | Poor |
| Comparative Test Example 5 | 5 | 0 | 4 | 0 | 4 | 0 | 4 | 0 | Poor |
| Comparative Test Example 6 | 3 | 0 | 2 | 0 | 3 | 0 | 3 | 0 | Poor |
| Comparative Test Example 7 | 3 | 0 | 2 | 0 | 3 | 0 | 3 | 0 | Poor |
| Comparative Test Example 8 | 3 | 0 | 2 | 0 | 3 | 0 | 3 | 0 | Poor |

TABLE 5

| Antigen: [2013-14 strain] | Activity of Influenza HA antigen | | | | | | | | |
|---|---|---|---|---|---|---|---|---|---|
| | H1N1/C | | H3N2/T | | B/M | | B/B | | |
| | Immediately after preparation | Two months later | Immediately after preparation | Two months later | Immediately after preparation | Two months later | Immediately after preparation | Two months later | Characteristics Two months later |
| Test Example 9 | 5 | 3 | 5 | 2 | 5 | 3 | 5 | 4 | Good |
| Test Example 10 | 5 | 4 | 5 | 4 | 5 | 4 | 5 | 4 | Poor |
| Test Example 11 | 5 | 4 | 5 | 3 | 5 | 4 | 5 | 4 | Poor |
| Test Example 12 | 5 | 4 | 5 | 3 | 5 | 4 | 5 | 4 | Poor |
| Test Example 13 | 5 | 4 | 5 | 4 | 2 | 1 | 3 | 1 | Poor |
| Test Example 14 | 5 | 3 | 3 | 3 | 2 | 1 | 4 | 1 | Poor |
| Test Example 15 | 4 | 3 | 5 | 4 | 2 | 1 | 5 | 3 | Poor |
| Test Example 16 | 5 | 4 | 5 | 4 | 4 | 3 | 5 | 2 | Poor |
| Comparative Test Example 9 | 2 | 0 | 1 | 0 | 1 | 0 | 2 | 0 | Poor |
| Comparative Test Example 10 | 5 | 0 | 5 | 0 | 4 | 0 | 4 | 0 | Poor |
| Comparative Test Example 11 | 5 | 0 | 4 | 0 | 4 | 0 | 4 | 0 | Poor |
| Comparative Test Example 12 | 5 | 0 | 4 | 0 | 4 | 0 | 4 | 0 | Poor |
| Comparative Test Example 13 | 5 | 0 | 4 | 0 | 4 | 0 | 4 | 0 | Poor |
| Comparative Test Example 14 | 3 | 0 | 2 | 0 | 3 | 0 | 3 | 0 | Poor |
| Comparative Test Example 15 | 3 | 0 | 2 | 0 | 3 | 0 | 3 | 0 | Poor |
| Comparative Test Example 16 | 3 | 0 | 2 | 0 | 3 | 0 | 3 | 0 | Poor |

As shown in Tables 4 and 5, the additives used in the test examples served as the stabilizers of the influenza HA antigens in the dried influenza vaccine preparations to show an effect of stabilizing specific influenza HA antigens. However, not all the influenza HA antigens were stabilized.

According to the test examples in which the additive containing an excipient was used, the excipient stabilized B/B antigen exclusively at a level of score 4, while the other influenza HA antigens were stabilized only at a level of score 2 or 3.

According to the test examples in which the additive containing a disaccharide was used, the disaccharide stabilized H1N1 antigen and antigens of type B at a level of 4, but failed to sufficiently stabilize H3N2 antigen. In contrast, according to the test examples in which the additive containing an amino acid was used, the arginine hydrochloride and lysine hydrochloride could stabilize HlN1 antigen and H3N2 antigen at a level of score 4 or higher, but failed to sufficiently stabilize antigens of type B. Threonine could stabilize H3N2 antigen at a level of score 4, but failed to sufficiently stabilize H1N1 antigen and antigens of type B. Proline could not stabilize any of the influenza HA antigens sufficiently.

Moreover, in relation to the characteristics of the dried influenza vaccine preparations, preparations containing the additive that contained an excipient could be used without specific inconvenience, but preparations containing a disaccharide or an amino acid alone did not have moldability and has inconvenience upon use thereof as a preparation.

The additive containing a disaccharide or amino acid used in the comparative test examples was confirmed to be not at all effective as a stabilizer for influenza HA antigens.

In addition, in Test Examples 2 and 10 in which trehalose was contained as a disaccharide compared to the other test examples in which isomalt or sucrose was contained, the stabilities of H3N2/V antigen and H3N2/T antigen were excellent, respectively.

<Evaluation of Stability of Lyophilized Tetravalent HA Vaccine Preparation>

EXAMPLE 1

An amount of 10% by mass of dextran, 5% by mass of trehalose, and 1% by mass of arginine hydrochloride were added to 34% by mass of purified water, and appropriately stirred to be dissolved. An amount of 50% by mass of the tetravalent vaccine solution A was added to the obtained solution, and mixed well. The obtained vaccine-containing preparation solution was dispensed in 0.25-g portions in vials for lyophilization, and lyophilized to prepare a dried influenza vaccine preparation. The obtained dried influenza vaccine preparation was stored at 40° C.±2° C. for six months, and the activity of the influenza HA antigen after the storage was measured by the SRID method. Also, the dried influenza vaccine preparation was evaluated in accordance with the characteristic evaluation method. The results were scored, and Table 8 shows the scores.

EXAMPLES 2 to 12, COMPARATIVE EXAMPLES 1 to 11

Solutions were prepared in accordance with the formulations shown in Table 6 in the same manner as in Example 1, and lyophilized to prepare dried influenza vaccine preparations. The obtained dried influenza vaccine preparations were stored at 40° C.±2° C. for six months, and the activity of each influenza HA antigen after the storage was measured by the SRID method. The dried influenza vaccine preparations were evaluated in accordance with the characteristic evaluation method. The results were scored, and Table 8 shows the scores.

EXAMPLE 13

An amount of 10% by mass of dextran, 5% by mass of trehalose, and 1% by mass of arginine hydrochloride were added to 34% by mass of purified water, and appropriately stirred to be dissolved. An amount of 50% by mass of the tetravalent vaccine solution B was added to the obtained solution, and mixed well. The obtained vaccine-containing preparation solution was dispensed in 0.25-g portions in vials for lyophilization, and lyophilized to prepare a dried influenza vaccine preparation. The obtained dried influenza vaccine preparation was stored at 40° C.±2° C. for six months, and the activity of the influenza HA antigen after the storage was measured by the SRID method. The dried influenza vaccine preparation was evaluated in accordance with the characteristic evaluation method. The results were scored, and Table 9 shows the scores.

EXAMPLES 14 to 24, COMPARATIVE EXAMPLES 12 to 22

Solutions were prepared in accordance with the formulations shown in Table 7 in the same manner as in Example 1, and lyophilized to prepare dried influenza vaccine preparations. The obtained dried influenza vaccine preparations were stored at 40° C.±2° C. for six months, and the activity of each influenza HA antigen after the storage was measured by the SRID method. The dried influenza vaccine preparations were evaluated in accordance with the characteristic evaluation method. The results were scored, and Table 9 shows the scores.

EXAMPLES 25 to 32, COMPARATIVE EXAMPLES 23 to 32

Solutions were prepared in accordance with the formulations shown in Table 10 in the same manner as in Example 1 except that hydroxypropyl cellulose (available from Nippon Soda Co., Ltd., product name: NISSO HPC SSL) or hydroxypropyl methylcellulose (available from Shin-Etsu Chemical Co., Ltd., product name: TC-5E) was used as the excipient instead of dextran, and lyophilized to prepare dried influenza vaccine preparations. The obtained dried influenza vaccine preparations were stored at 40° C.±2° C. for six months, and the activity of each influenza HA antigen after the storage was measured by the SRID method. The dried influenza vaccine preparations were evaluated in accordance with the characteristic evaluation method. The results were scored, and Table 12 shows the scores.

EXAMPLES 33 to 40, COMPARATIVE EXAMPLES 33 to 42

Solutions were prepared in accordance with the formulations shown in Table 11 in the same manner as in Example 13 except that hydroxypropyl cellulose or hydroxypropyl methylcellulose was used as the excipient instead of dextran, and lyophilized to prepare dried influenza vaccine preparations. The obtained dried influenza vaccine preparations were stored at 40° C.+2° C. for six months, and the activity of each influenza HA antigen after the storage was measured by the SRID method. The dried influenza vaccine preparations were evaluated in accordance with the characteristic evaluation method. The results were scored, and Table 13 shows the scores.

TABLE 6

| | Formulation [% by mass] | | | | | | | | | | | | | | | | | | | | | |
|---|---|---|---|---|---|---|---|---|---|---|---|---|---|---|---|---|---|---|---|---|---|---|
| | Example | | | | | | | | | | | | Comparative Example | | | | | | | | | | |
| Component | 1 | 2 | 3 | 4 | 5 | 6 | 7 | 8 | 9 | 10 | 11 | 12 | 1 | 2 | 3 | 4 | 5 | 6 | 7 | 8 | 9 | 10 | 11 |
| Tetravalent vaccine solution A | 50 | 50 | 50 | 50 | 50 | 50 | 50 | 50 | 50 | 50 | 50 | 50 | 50 | 50 | 50 | 50 | 50 | 50 | 50 | 50 | 50 | 50 | 50 |
| Dextran | 10 | 10 | 10 | 10 | 10 | 10 | 10 | 10 | 10 | 10 | 10 | 10 | 16 | 11 | 11 | 11 | 15 | 15 | 15 | 15 | — | — | — |
| Trehalose | 5 | 5 | 5 | 5 | — | — | — | — | — | — | — | — | — | 5 | — | — | — | — | — | — | 5 | — | — |
| Isomalt | — | — | — | — | 5 | 5 | 5 | 5 | — | — | — | — | — | — | 5 | — | — | — | — | — | — | 5 | — |
| Sucrose | — | — | — | — | — | — | — | — | 5 | 5 | 5 | 5 | — | — | — | 5 | — | — | — | — | — | — | 5 |
| Arginine hydrochloride | 1 | — | — | — | 1 | — | — | — | 1 | — | — | — | — | — | — | — | 1 | — | — | — | 1 | 1 | 1 |
| Proline | — | 1 | — | — | — | 1 | — | — | — | 1 | — | — | — | — | — | — | — | 1 | — | — | — | — | — |
| Threonine | — | — | 1 | — | — | — | 1 | — | — | — | 1 | — | — | — | — | — | — | — | 1 | — | — | — | — |
| Lysine hydrochloride | — | — | — | 1 | — | — | — | 1 | — | — | — | 1 | — | — | — | — | — | — | — | 1 | — | — | — |
| Purified water | 34 | 34 | 34 | 34 | 34 | 34 | 34 | 34 | 34 | 34 | 34 | 34 | 34 | 34 | 34 | 34 | 34 | 34 | 34 | 34 | 44 | 44 | 44 |

TABLE 7

| | Formulation [% by mass] | | | | | | | | | | | | | | | | | | | | | |
|---|---|---|---|---|---|---|---|---|---|---|---|---|---|---|---|---|---|---|---|---|---|---|
| | Example | | | | | | | | | | | | Comparative Example | | | | | | | | | | |
| Component | 13 | 14 | 15 | 16 | 17 | 18 | 19 | 20 | 21 | 22 | 23 | 24 | 12 | 13 | 14 | 15 | 16 | 17 | 18 | 19 | 20 | 21 | 22 |
| Tetravalent vaccine solution B | 50 | 50 | 50 | 50 | 50 | 50 | 50 | 50 | 50 | 50 | 50 | 50 | 50 | 50 | 50 | 50 | 50 | 50 | 50 | 50 | 50 | 50 | 50 |
| Dextran | 10 | 10 | 10 | 10 | 10 | 10 | 10 | 10 | 10 | 10 | 10 | 10 | 16 | 11 | 11 | 11 | 15 | 15 | 15 | 15 | — | — | — |
| Trehalose | 5 | 5 | 5 | 5 | — | — | — | — | — | — | — | — | — | 5 | — | — | — | — | — | — | 5 | — | — |
| Isomalt | — | — | — | — | 5 | 5 | 5 | 5 | — | — | — | — | — | — | 5 | — | — | — | — | — | — | 5 | — |
| Sucrose | — | — | — | — | — | — | — | — | 5 | 5 | 5 | 5 | — | — | — | 5 | — | — | — | — | — | — | 5 |
| Arginine hydrochloride | 1 | — | — | — | 1 | — | — | — | 1 | — | — | — | — | — | — | — | 1 | — | — | — | 1 | 1 | 1 |
| Proline | — | 1 | — | — | — | 1 | — | — | — | 1 | — | — | — | — | — | — | — | 1 | — | — | — | — | — |
| Threonine | — | — | 1 | — | — | — | 1 | — | — | — | 1 | — | — | — | — | — | — | — | 1 | — | — | — | — |
| Lysine hydrochloride | — | — | — | 1 | — | — | — | 1 | — | — | — | 1 | — | — | — | — | — | — | — | 1 | — | — | — |
| Purified water | 34 | 34 | 34 | 34 | 34 | 34 | 34 | 34 | 34 | 34 | 34 | 34 | 34 | 34 | 34 | 34 | 34 | 34 | 34 | 34 | 44 | 44 | 44 |

TABLE 8

| Antigen: [2012-13 strain] | Activity of Influenza HA antigen H1N1/C Immediately after preparation | H1N1/C Two months later | H1N1/C Four months later | H1N1/C Six months later | H3N2/V Immediately after preparation | H3N2/V Two months later | H3N2/V Four months later | H3N2/V Six months later | B/W Immediately after preparation | B/W Two months later | B/W Four months later | B/W Six months later |
|---|---|---|---|---|---|---|---|---|---|---|---|---|
| Example 1 | 5 | 5 | 5 | 5 | 5 | 5 | 5 | 5 | 5 | 5 | 5 | 5 |
| Example 2 | 5 | 5 | 5 | 5 | 5 | 5 | 5 | 4 | 5 | 5 | 5 | 5 |
| Example 3 | 5 | 5 | 5 | 5 | 5 | 5 | 5 | 4 | 5 | 5 | 5 | 5 |
| Example 4 | 5 | 5 | 5 | 5 | 5 | 5 | 5 | 4 | 5 | 5 | 5 | 5 |
| Example 5 | 5 | 5 | 5 | 4 | 5 | 5 | 5 | 4 | 5 | 5 | 5 | 5 |
| Example 6 | 5 | 5 | 5 | 4 | 5 | 5 | 5 | 4 | 5 | 5 | 5 | 4 |
| Example 7 | 5 | 5 | 5 | 4 | 5 | 5 | 5 | 4 | 5 | 5 | 5 | 4 |
| Example 8 | 5 | 5 | 5 | 4 | 5 | 5 | 5 | 4 | 5 | 5 | 5 | 4 |
| Example 9 | 5 | 5 | 4 | 4 | 5 | 5 | 5 | 4 | 5 | 5 | 4 | 4 |
| Example 10 | 5 | 5 | 4 | 4 | 5 | 5 | 5 | 4 | 5 | 5 | 4 | 4 |
| Example 11 | 5 | 5 | 4 | 4 | 5 | 5 | 5 | 4 | 5 | 5 | 4 | 4 |
| Example 12 | 5 | 5 | 4 | 4 | 5 | 5 | 5 | 4 | 5 | 5 | 4 | 4 |
| Comparative Example 1 | 5 | 3 | 0 | 0 | 5 | 3 | 1 | 0 | 5 | 2 | 0 | 0 |
| Comparative Example 2 | 5 | 4 | 3 | 3 | 5 | 4 | 3 | 2 | 5 | 4 | 3 | 3 |
| Comparative Example 3 | 5 | 4 | 3 | 2 | 5 | 4 | 3 | 2 | 5 | 4 | 3 | 3 |
| Comparative Example 4 | 5 | 4 | 2 | 2 | 5 | 4 | 3 | 2 | 5 | 4 | 2 | 2 |
| Comparative Example 5 | 5 | 5 | 4 | 3 | 5 | 5 | 4 | 4 | 5 | 4 | 2 | 2 |
| Comparative Example 6 | 5 | 4 | 3 | 2 | 5 | 4 | 4 | 3 | 5 | 4 | 2 | 2 |
| Comparative Example 7 | 5 | 4 | 3 | 2 | 5 | 4 | 4 | 3 | 5 | 4 | 2 | 2 |
| Comparative Example 8 | 5 | 4 | 3 | 2 | 5 | 4 | 4 | 3 | 5 | 4 | 2 | 2 |
| Comparative Example 9 | 5 | 4 | 4 | 3 | 5 | 4 | 4 | 4 | 5 | 4 | 3 | 3 |
| Comparative Example 10 | 5 | 4 | 3 | 2 | 5 | 4 | 4 | 3 | 5 | 4 | 3 | 3 |
| Comparative Example 11 | 5 | 4 | 3 | 2 | 5 | 4 | 4 | 3 | 5 | 4 | 3 | 2 |

| Antigen: [2012-13 strain] | Activity of Influenza HA antigen B/B Immediately after preparation | B/B Two months later | B/B Four months later | B/B Six months later | Characteristics Immediately after preparation | Characteristics Six months later |
|---|---|---|---|---|---|---|
| Example 1 | 5 | 5 | 5 | 5 | Good | Good |
| Example 2 | 5 | 5 | 5 | 5 | Good | Good |
| Example 3 | 5 | 5 | 5 | 5 | Good | Good |
| Example 4 | 5 | 5 | 5 | 5 | Good | Good |
| Example 5 | 5 | 5 | 5 | 5 | Good | Good |
| Example 6 | 5 | 5 | 5 | 4 | Good | Good |
| Example 7 | 5 | 5 | 5 | 4 | Good | Good |
| Example 8 | 5 | 5 | 5 | 4 | Good | Good |
| Example 9 | 5 | 5 | 5 | 4 | Good | Good |
| Example 10 | 5 | 5 | 5 | 4 | Good | Good |
| Example 11 | 5 | 5 | 5 | 4 | Good | Good |
| Example 12 | 5 | 5 | 5 | 4 | Good | Good |
| Comparative Example 1 | 5 | 4 | 3 | 3 | Good | Good |
| Comparative Example 2 | 5 | 4 | 4 | 3 | Good | Good |
| Comparative Example 3 | 5 | 4 | 4 | 3 | Good | Good |
| Comparative Example 4 | 5 | 4 | 3 | 3 | Good | Good |
| Comparative Example 5 | 5 | 5 | 4 | 3 | Good | Good |
| Comparative Example 6 | 5 | 4 | 4 | 3 | Good | Good |
| Comparative Example 7 | 5 | 4 | 4 | 3 | Good | Good |
| Comparative Example 8 | 5 | 4 | 4 | 3 | Good | Good |
| Comparative Example 9 | 5 | 4 | 4 | 3 | Poor | Poor |
| Comparative Example 10 | 5 | 4 | 4 | 3 | Poor | Poor |
| Comparative Example 11 | 5 | 4 | 4 | 3 | Poor | Poor |

TABLE 9

| Antigen: [2013-14 strain] | Activity of Influenza HA antigen H1N1/C Immediately after preparation | H1N1/C Two months later | H1N1/C Four months later | H1N1/C Six months later | H3N2/T Immediately after preparation | H3N2/T Two months later | H3N2/T Four months later | H3N2/T Six months later | B/M Immediately after preparation | B/M Two months later | B/M Four months later | B/M Six months later |
|---|---|---|---|---|---|---|---|---|---|---|---|---|
| Example 13 | 5 | 5 | 5 | 5 | 5 | 5 | 5 | 5 | 5 | 5 | 5 | 5 |
| Example 14 | 5 | 5 | 5 | 5 | 5 | 5 | 5 | 4 | 5 | 5 | 5 | 5 |
| Example 15 | 5 | 5 | 5 | 5 | 5 | 5 | 5 | 4 | 5 | 5 | 5 | 5 |
| Example 16 | 5 | 5 | 5 | 5 | 5 | 5 | 5 | 4 | 5 | 5 | 5 | 5 |
| Example 17 | 5 | 5 | 5 | 4 | 5 | 5 | 5 | 4 | 5 | 5 | 5 | 5 |
| Example 18 | 5 | 5 | 5 | 4 | 5 | 5 | 5 | 4 | 5 | 5 | 5 | 4 |
| Example 19 | 5 | 5 | 5 | 4 | 5 | 5 | 5 | 4 | 5 | 5 | 5 | 4 |
| Example 20 | 5 | 5 | 5 | 4 | 5 | 5 | 5 | 4 | 5 | 5 | 5 | 4 |
| Example 21 | 5 | 5 | 4 | 4 | 5 | 5 | 5 | 4 | 5 | 5 | 4 | 4 |
| Example 22 | 5 | 5 | 4 | 4 | 5 | 5 | 5 | 4 | 5 | 5 | 4 | 4 |
| Example 23 | 5 | 5 | 4 | 4 | 5 | 5 | 5 | 4 | 5 | 5 | 4 | 4 |
| Example 24 | 5 | 5 | 4 | 4 | 5 | 5 | 5 | 4 | 5 | 5 | 4 | 4 |
| Comparativ Example 12 | 5 | 3 | 0 | 0 | 5 | 3 | 2 | 0 | 5 | 3 | 2 | 0 |
| Comparativ Example 13 | 5 | 5 | 3 | 3 | 5 | 4 | 3 | 2 | 5 | 4 | 3 | 3 |
| Comparativ Example 14 | 5 | 4 | 3 | 2 | 5 | 4 | 3 | 2 | 5 | 4 | 3 | 3 |
| Comparativ Example 15 | 5 | 4 | 2 | 2 | 5 | 4 | 3 | 2 | 5 | 4 | 2 | 2 |
| Comparativ Example 16 | 5 | 5 | 4 | 3 | 5 | 5 | 4 | 4 | 5 | 4 | 2 | 2 |
| Comparativ Example 17 | 5 | 4 | 3 | 2 | 5 | 4 | 4 | 3 | 5 | 4 | 2 | 2 |
| Comparativ Example 18 | 5 | 4 | 3 | 2 | 5 | 4 | 4 | 3 | 5 | 4 | 2 | 2 |
| Comparativ Example 19 | 5 | 4 | 3 | 2 | 5 | 4 | 4 | 3 | 5 | 4 | 2 | 2 |
| Comparativ Example 20 | 5 | 4 | 3 | 3 | 5 | 4 | 4 | 4 | 5 | 4 | 3 | 3 |
| Comparativ Example 21 | 5 | 4 | 3 | 2 | 5 | 4 | 4 | 3 | 5 | 4 | 3 | 3 |
| Comparativ Example 22 | 5 | 4 | 3 | 2 | 5 | 4 | 4 | 3 | 5 | 4 | 3 | 2 |

| Antigen: [2013-14 strain] | Activity of Influenza HA antigen B/B Immediately after preparation | B/B Two months later | B/B Four months later | B/B Six months later | Characteristics Immediately after preparation | Characteristics Four months later |
|---|---|---|---|---|---|---|
| Example 13 | 5 | 5 | 5 | 5 | Good | Good |
| Example 14 | 5 | 5 | 5 | 5 | Good | Good |
| Example 15 | 5 | 5 | 5 | 5 | Good | Good |
| Example 16 | 5 | 5 | 5 | 5 | Good | Good |
| Example 17 | 5 | 5 | 5 | 5 | Good | Good |
| Example 18 | 5 | 5 | 5 | 4 | Good | Good |
| Example 19 | 5 | 5 | 5 | 4 | Good | Good |
| Example 20 | 5 | 5 | 5 | 4 | Good | Good |
| Example 21 | 5 | 5 | 5 | 4 | Good | Good |
| Example 22 | 5 | 5 | 5 | 4 | Good | Good |
| Example 23 | 5 | 5 | 5 | 4 | Good | Good |
| Example 24 | 5 | 5 | 5 | 4 | Good | Good |
| Comparativ Example 12 | 5 | 4 | 3 | 3 | Good | Good |
| Comparativ Example 13 | 5 | 5 | 4 | 3 | Good | Good |
| Comparativ Example 14 | 5 | 4 | 4 | 3 | Good | Good |
| Comparativ Example 15 | 5 | 4 | 3 | 3 | Good | Good |
| Comparativ Example 16 | 5 | 5 | 4 | 3 | Good | Good |
| Comparativ Example 17 | 5 | 4 | 4 | 3 | Good | Good |
| Comparativ Example 18 | 5 | 4 | 4 | 3 | Good | Good |
| Comparativ Example 19 | 5 | 4 | 4 | 3 | Good | Good |
| Comparativ Example 20 | 5 | 4 | 4 | 3 | Poor | Poor |
| Comparativ Example 21 | 5 | 4 | 4 | 3 | Poor | Poor |
| Comparativ Example 22 | 5 | 4 | 4 | 3 | Poor | Poor |

TABLE 10

| Component | Formulation [% by mass] | | | | | | | | | | | | | | | | | |
|---|---|---|---|---|---|---|---|---|---|---|---|---|---|---|---|---|---|---|
| | Example | | | | | | | | Comparative Example | | | | | | | | | |
| | 25 | 26 | 27 | 28 | 29 | 30 | 31 | 32 | 23 | 24 | 25 | 26 | 27 | 28 | 29 | 30 | 31 | 32 |
| Tetravalent vaccine solution A | 50 | 50 | 50 | 50 | 50 | 50 | 50 | 50 | 50 | 50 | 50 | 50 | 50 | 50 | 50 | 50 | 50 | 50 |
| HPC-SSL | 10 | 10 | 10 | 10 | — | — | — | — | 16 | 11 | 11 | 11 | 15 | — | — | — | — | — |
| HPMC | — | — | — | — | 10 | 10 | 10 | 10 | — | — | — | — | — | 16 | 11 | 11 | 11 | 15 |
| Trehalose | 5 | 5 | — | — | 5 | 5 | — | — | — | 5 | — | — | — | — | 5 | — | — | — |
| Isomalt | — | — | 5 | 5 | — | — | 5 | 5 | — | — | 5 | — | — | — | — | 5 | — | — |
| Arginine hydrochloride | 1 | — | 1 | — | 1 | — | 1 | — | — | — | — | 1 | — | — | — | — | 1 | — |
| Lysine hydrochloride | — | 1 | — | 1 | — | 1 | — | 1 | — | — | — | — | 1 | — | — | — | — | 1 |
| Purified water | 34 | 34 | 34 | 34 | 34 | 34 | 34 | 34 | 34 | 34 | 34 | 38 | 34 | 34 | 34 | 34 | 38 | 34 |

TABLE 11

| Component | Formulation [% by mass] | | | | | | | | | | | | | | | | | |
|---|---|---|---|---|---|---|---|---|---|---|---|---|---|---|---|---|---|---|
| | Example | | | | | | | | Comparative Example | | | | | | | | | |
| | 33 | 34 | 35 | 36 | 37 | 38 | 39 | 40 | 33 | 34 | 35 | 36 | 37 | 38 | 39 | 40 | 41 | 42 |
| Tetravalent vaccine solution B | 50 | 50 | 50 | 50 | 50 | 50 | 50 | 50 | 50 | 50 | 50 | 50 | 50 | 50 | 50 | 50 | 50 | 50 |
| HPC-SSL | 10 | 10 | 10 | 10 | — | — | — | — | 16 | 11 | 11 | 11 | 15 | — | — | — | — | — |
| HPMC | — | — | — | — | 10 | 10 | 10 | 10 | — | — | — | — | — | 16 | 11 | 11 | 11 | 15 |
| Trehalose | 5 | 5 | — | — | 5 | 5 | — | — | — | 5 | — | — | — | — | 5 | — | — | — |
| Isomalt | — | — | 5 | 5 | — | — | 5 | 5 | — | — | 5 | — | — | — | — | 5 | — | — |
| Arginine hydrochloride | 1 | — | 1 | — | 1 | — | 1 | — | — | — | — | 1 | — | — | — | — | 1 | — |
| Lysine hydrochloride | — | 1 | — | 1 | — | 1 | — | 1 | — | — | — | — | 1 | — | — | — | — | 1 |
| Purified water | 34 | 34 | 34 | 34 | 34 | 34 | 34 | 34 | 34 | 34 | 34 | 38 | 34 | 34 | 34 | 34 | 38 | 34 |

TABLE 12

| Antigen: [2012-13 strain] | Activity of influenza HA antigen | | | | | | | | | |
|---|---|---|---|---|---|---|---|---|---|---|
| | H1N1/C | | | | H3N2/V | | | | B/W | |
| | Immediately after preparation | Two months later | Four months later | Six months later | Immediately after preparation | Two months later | Four months later | Six months later | Immediately after preparation | Two months later |
| Example 25 | 5 | 5 | 5 | 4 | 5 | 5 | 5 | 4 | 5 | 5 |
| Example 26 | 5 | 5 | 5 | 4 | 5 | 5 | 5 | 4 | 5 | 5 |
| Example 27 | 5 | 5 | 5 | 4 | 5 | 5 | 5 | 4 | 5 | 5 |
| Example 28 | 5 | 5 | 5 | 4 | 5 | 5 | 5 | 4 | 5 | 5 |
| Example 29 | 5 | 5 | 5 | 4 | 5 | 5 | 5 | 4 | 5 | 5 |
| Example 30 | 5 | 5 | 5 | 4 | 5 | 5 | 5 | 4 | 5 | 5 |
| Example 31 | 5 | 5 | 5 | 4 | 5 | 5 | 5 | 4 | 5 | 5 |
| Example 32 | 5 | 5 | 5 | 4 | 5 | 5 | 5 | 4 | 5 | 5 |
| Comparative Example 23 | 5 | 0 | 0 | 0 | 5 | 0 | 0 | 0 | 5 | 0 |
| Comparative Example 24 | 5 | 4 | 3 | 3 | 5 | 4 | 3 | 2 | 5 | 4 |
| Comparative Example 25 | 5 | 4 | 3 | 2 | 5 | 4 | 3 | 2 | 5 | 4 |
| Comparative Example 26 | 5 | 4 | 0 | 0 | 5 | 4 | 0 | 0 | 5 | 3 |
| Comparative Example 27 | 5 | 4 | 0 | 0 | 5 | 4 | 0 | 0 | 5 | 3 |
| Comparative Example 28 | 5 | 0 | 0 | 0 | 5 | 0 | 0 | 0 | 5 | 0 |
| Comparative Example 29 | 5 | 4 | 3 | 3 | 5 | 4 | 3 | 2 | 5 | 4 |
| Comparative Example 30 | 5 | 4 | 3 | 2 | 5 | 4 | 3 | 2 | 5 | 4 |
| Comparative Example 31 | 5 | 4 | 3 | 3 | 5 | 4 | 4 | 3 | 5 | 3 |
| Comparative Example 32 | 5 | 4 | 3 | 3 | 5 | 4 | 3 | 3 | 5 | 3 |

| Antigen: [2012-13 strain] | Activity of influenza HA antigen | | | | | | Characteristics | |
|---|---|---|---|---|---|---|---|---|
| | B/W | | B/B | | | | | |
| | Four months later | Six months later | Immediately after preparation | Two months later | Four months later | Six months later | Immediately after preparation | Six months later |
| Example 25 | 5 | 4 | 5 | 5 | 5 | 4 | Good | Good |
| Example 26 | 5 | 4 | 5 | 5 | 5 | 4 | Good | Good |

TABLE 12-continued

| | | | | | | | | |
|---|---|---|---|---|---|---|---|---|
| Example 27 | 5 | 4 | 5 | 5 | 5 | 4 | Good | Good |
| Example 28 | 5 | 4 | 5 | 5 | 5 | 4 | Good | Good |
| Example 29 | 5 | 4 | 5 | 5 | 5 | 4 | Good | Good |
| Example 30 | 5 | 4 | 5 | 5 | 5 | 4 | Good | Good |
| Example 31 | 5 | 4 | 5 | 5 | 5 | 4 | Good | Good |
| Example 32 | 5 | 4 | 5 | 5 | 5 | 4 | Good | Good |
| Comparative Example 23 | 0 | 0 | 5 | 0 | 0 | 0 | Good | Good |
| Comparative Example 24 | 3 | 3 | 5 | 4 | 4 | 3 | Good | Good |
| Comparative Example 25 | 3 | 3 | 5 | 4 | 4 | 3 | Good | Good |
| Comparative Example 26 | 0 | 0 | 5 | 4 | 0 | 0 | Good | Good |
| Comparative Example 27 | 0 | 0 | 5 | 4 | 0 | 0 | Good | Good |
| Comparative Example 28 | 0 | 0 | 5 | 0 | 0 | 0 | Good | Good |
| Comparative Example 29 | 3 | 3 | 5 | 4 | 4 | 3 | Good | Good |
| Comparative Example 30 | 3 | 3 | 5 | 4 | 4 | 3 | Good | Good |
| Comparative Example 31 | 0 | 0 | 5 | 4 | 0 | 0 | Good | Good |
| Comparative Example 32 | 0 | 0 | 5 | 4 | 0 | 0 | Good | Good |

TABLE 13

| | Activity of influenza HA antigen | | | | | | | | | |
|---|---|---|---|---|---|---|---|---|---|---|
| | H1N1/C | | | | H3N2/T | | | | B/M | |
| Antigen: [2013-14 strain] | Immediately after preparation | Two months later | Four months later | Six months later | Immediately after preparation | Two months later | Four months later | Six months later | Immediately after preparation | Two months later |
| Example 33 | 5 | 5 | 5 | 4 | 5 | 5 | 5 | 4 | 5 | 5 |
| Example 34 | 5 | 5 | 5 | 4 | 5 | 5 | 5 | 4 | 5 | 5 |
| Example 35 | 5 | 5 | 5 | 4 | 5 | 5 | 5 | 4 | 5 | 5 |
| Example 36 | 5 | 5 | 5 | 4 | 5 | 5 | 5 | 4 | 5 | 5 |
| Example 37 | 5 | 5 | 5 | 4 | 5 | 5 | 5 | 4 | 5 | 5 |
| Example 38 | 5 | 5 | 5 | 4 | 5 | 5 | 5 | 4 | 5 | 5 |
| Example 39 | 5 | 5 | 5 | 4 | 5 | 5 | 5 | 4 | 5 | 5 |
| Example 40 | 5 | 5 | 5 | 4 | 5 | 5 | 5 | 4 | 5 | 5 |
| Comparative Example 33 | 5 | 0 | 0 | 0 | 5 | 0 | 0 | 0 | 5 | 0 |
| Comparative Example 34 | 5 | 4 | 3 | 3 | 5 | 4 | 3 | 2 | 5 | 4 |
| Comparative Example 35 | 5 | 4 | 3 | 2 | 5 | 4 | 3 | 2 | 5 | 4 |
| Comparative Example 36 | 5 | 4 | 0 | 0 | 5 | 4 | 0 | 0 | 5 | 3 |
| Comparative Example 37 | 5 | 4 | 0 | 0 | 5 | 4 | 0 | 0 | 5 | 3 |
| Comparative Example 38 | 5 | 0 | 0 | 0 | 5 | 0 | 0 | 0 | 5 | 0 |
| Comparative Example 39 | 5 | 4 | 3 | 3 | 5 | 4 | 3 | 2 | 5 | 4 |
| Comparative Example 40 | 5 | 4 | 3 | 2 | 5 | 4 | 3 | 2 | 5 | 4 |
| Comparative Example 41 | 5 | 4 | 3 | 3 | 5 | 4 | 4 | 3 | 5 | 3 |
| Comparative Example 42 | 5 | 4 | 3 | 3 | 5 | 4 | 3 | 3 | 5 | 3 |

| | Activity of influenza HA antigen | | | | | | | |
|---|---|---|---|---|---|---|---|---|
| | B/M | | B/B | | | | Characteristics | |
| Antigen: [2013-14 strain] | Four months later | Six months later | Immediately after preparation | Two months later | Four months later | Six months later | Immediately after preparation | Four months later |
| Example 33 | 5 | 4 | 5 | 5 | 5 | 4 | Good | Good |
| Example 34 | 5 | 4 | 5 | 5 | 5 | 4 | Good | Good |
| Example 35 | 5 | 4 | 5 | 5 | 5 | 4 | Good | Good |
| Example 36 | 5 | 4 | 5 | 5 | 5 | 4 | Good | Good |
| Example 37 | 5 | 4 | 5 | 5 | 5 | 4 | Good | Good |
| Example 38 | 5 | 4 | 5 | 5 | 5 | 4 | Good | Good |
| Example 39 | 5 | 4 | 5 | 5 | 5 | 4 | Good | Good |
| Example 40 | 5 | 4 | 5 | 5 | 5 | 4 | Good | Good |
| Comparative Example 33 | 0 | 0 | 5 | 0 | 0 | 0 | Good | Good |
| Comparative Example 34 | 3 | 3 | 5 | 4 | 4 | 3 | Good | Good |
| Comparative Example 35 | 3 | 3 | 5 | 4 | 4 | 3 | Good | Good |
| Comparative Example 36 | 0 | 0 | 5 | 4 | 0 | 0 | Good | Good |
| Comparative Example 37 | 0 | 0 | 5 | 4 | 0 | 0 | Good | Good |
| Comparative Example 38 | 0 | 0 | 5 | 0 | 0 | 0 | Good | Good |
| Comparative Example 39 | 3 | 3 | 5 | 4 | 4 | 3 | Good | Good |
| Comparative Example 40 | 3 | 3 | 5 | 4 | 4 | 3 | Good | Good |
| Comparative Example 41 | 0 | 0 | 5 | 4 | 0 | 0 | Good | Good |
| Comparative Example 42 | 0 | 0 | 5 | 4 | 0 | 0 | Good | Good |

In Examples 1 to 40 in which an excipient, a disaccharide, and an amino acid were contained, the characteristics of the dried influenza vaccine preparation and the stabilities of the influenza HA antigens were favorable.

In contrast, in Comparative Examples 9 to 11 and 20 to 22 in which no excipient was used, the characteristics of the dried influenza vaccine preparation was poor and the stability of the influenza HA antigen of any type tended to be lowered after storage for two months.

In Comparative Examples 2 to 4 and 13 to 15 in which no amino acid was used, the characteristics of the dried influenza vaccine preparation was favorable but the stability of the influenza HA antigen of any type tended to be lowered after storage for two months.

In Comparative Examples 5 to 8 and 16 to 19 in which no disaccharide was used, the characteristics were favorable but the stability of the influenza HA antigen tended to be lowered after storage for two months.

These results show that an excipient is necessity for imparting favorable characteristics to the dried influenza vaccine preparation, contributes to stabilization of the activity of the influenza HA antigen, and improves the stability of the activity of the influenza HA antigen when used together with an amino acid and a disaccharide.

Among Examples 1 to 24 in which an excipient was used, the stability of the activity of the influenza HA antigen after storage for four to six months was particularly favorable in Examples 1 to 4 and 13 to 16 in which trehalose was used as a disaccharide, compared to Examples 5 to 12 and 17 to 24 in which another disaccharide was used.

Among the examples in which trehalose was used as a disaccharide, the stability of the activity of the influenza HA antigen after storage of the preparation containing H3N2 antigen for six months was particularly favorable in Examples 1 and 13 in which arginine hydrochloride was used, compared to Examples 2 to 4 and 14 to 16 in which another amino acid was used.

These results show that the use of an excipient, arginine hydrochloride as an amino acid, and trehalose as a disaccharide particularly improves the stability of the activity of the influenza HA antigen.

The same tendency was shown also in Examples 25 to 32 and Comparative Examples 23 to 32 and in Examples 33 to 40 and Comparative Examples 33 to 42 in which hydroxypropyl cellulose or hydroxypropyl methylcellulose was used as an excipient. In other words, in these comparative examples in which no amino acid or disaccharide was used, the stability of the activity of the influenza HA antigen tended to be lowered after storage for two months.

In Examples 25 to 32 and 33 to 40 in which hydroxypropyl cellulose or hydroxypropyl methylcellulose was used as an excipient, the stability of the activity of the influenza HA antigen tended to be lowered after storage for six months.

In contrast, in Examples 1, 4, 13, and 16 in which dextran was used as an excipient, trehalose was used as a disaccharide, and arginine or lysine was used as an amino acid, the activity was sufficiently stabilized after storage of the preparation containing H1N1 antigen, B/W antigen, or B/B antigen for six months.

In particular, in Examples 1 and 13 in which arginine hydrochloride was used as an amino acid, the activity of the influenza HA antigen was sufficiently stabilized after storage of the preparation containing H3N2 antigen for six months.

These results show that the use of dextran as an excipient, arginine hydrochloride as an amino acid, and trehalose as a disaccharide sufficiently stabilizes the activity of the influenza HA antigens of all the types. The dried influenza vaccine preparations according to Examples 1 to 40 and Comparative Examples 1 to 42 were all low-moisture-content dried preparations having a moisture content measured by the loss on drying test of 10% by mass or less.

COMPARATIVE EXAMPLES 43 to 48 and EXAMPLES 41 to 48)

Solutions were prepared in accordance with the formulations shown in Table 14 in the same manner as in Example 1, and lyophilized to prepare dried influenza vaccine preparations. The obtained dried influenza vaccine preparations were stored at 40° C.±2° C. for four months, and the activity of the influenza HA antigen after the storage was measured by the SRID method. The dried influenza vaccine preparations were evaluated in accordance with the characteristic evaluation method. The results were scored, and Tables 15 and 16 show the scores.

TABLE 14

| | Formulation [% by mass] | | | | | | | | | | | | | |
|---|---|---|---|---|---|---|---|---|---|---|---|---|---|---|
| | Comparative Example | | | Example | | | | Comparative Example | | | Example | | | |
| Component | 43 | 44 | 45 | 41 | 42 | 43 | 44 | 46 | 47 | 48 | 45 | 46 | 47 | 48 |
| Tetravalent vaccine solution A | 50 | 50 | 50 | 50 | 50 | 50 | 50 | — | — | — | — | — | — | — |
| Tetravalent vaccine solution B | — | — | — | — | — | — | — | 50 | 50 | 50 | 50 | 50 | 50 | 50 |
| Dextran | 10 | 10 | 10 | 10 | 10 | 10 | 10 | 10 | 10 | 10 | 10 | 10 | 10 | 10 |
| Trehalose | — | — | — | 5 | 5 | 5 | 5 | — | — | — | 5 | 5 | 5 | 5 |
| Glucose | 5 | — | — | — | — | — | — | 5 | — | — | — | — | — | — |
| Galactose | — | 5 | — | — | — | — | — | — | 5 | — | — | — | — | — |
| Fructose | — | — | 5 | — | — | — | — | — | — | 5 | — | — | — | — |
| Arginine hydrochloride | 1 | 1 | 1 | — | — | — | — | 1 | 1 | 1 | — | — | — | — |
| Alanine | — | — | — | 1 | — | — | — | — | — | — | 1 | — | — | — |
| Valine | — | — | — | — | 1 | — | — | — | — | — | — | 1 | — | — |
| Isoleucine | — | — | — | — | — | 1 | — | — | — | — | — | — | 1 | — |
| Leucine | — | — | — | — | — | — | 1 | — | — | — | — | — | — | 1 |
| Purified water | 34 | 34 | 34 | 34 | 34 | 34 | 34 | 34 | 34 | 34 | 34 | 34 | 34 | 34 |

TABLE 15

| | Activity of influenza HA antigen | | | | | | | | |
|---|---|---|---|---|---|---|---|---|---|
| | H1N1/C | | | H3N2/V | | | B/W | | |
| Antigen: [2012-13 strain] | Immediately after preparation | Two months later | Four months later | Immediately after preparation | Two months later | Four months later | Immediately after preparation | Two months later | Four months later |
| Comparative Example 43 | 5 | 4 | 4 | 5 | 4 | 2 | 5 | 4 | 2 |
| Comparative Example 44 | 5 | 4 | 4 | 5 | 4 | 2 | 5 | 4 | 2 |
| Comparative Example 45 | 5 | 4 | 4 | 5 | 4 | 2 | 5 | 4 | 2 |
| Example 41 | 5 | 3 | 1 | 5 | 3 | 1 | 5 | 3 | 1 |
| Example 42 | 5 | 3 | 1 | 5 | 3 | 1 | 5 | 3 | 1 |
| Example 42 | 5 | 3 | 1 | 5 | 3 | 1 | 5 | 3 | 1 |
| Example 44 | 5 | 3 | 1 | 5 | 3 | 1 | 5 | 3 | 1 |

| | Activity of influenza HA antigen B/B | | | Characteristics | |
|---|---|---|---|---|---|
| Antigen: [2012-13 strain] | Immediately after preparation | Two months later | Four months later | Immediately after preparation | Four months later |
| Comparative Example 43 | 5 | 4 | 4 | Good | Good |
| Comparative Example 44 | 5 | 4 | 4 | Good | Good |
| Comparative Example 45 | 5 | 4 | 4 | Good | Good |
| Example 41 | 5 | 4 | 3 | Good | Good |
| Example 42 | 5 | 4 | 3 | Good | Good |
| Example 42 | 5 | 4 | 3 | Good | Good |
| Example 44 | 5 | 4 | 3 | Good | Good |

TABLE 16

| | Activity of influenza HA antigen | | | | | | | | | | | | Characteristics | |
|---|---|---|---|---|---|---|---|---|---|---|---|---|---|---|
| | H1N1/C | | | H3N2/T | | | B/M | | | B/B | | | | |
| Antigen: [2013-14 strain] | Immediately after preparation | Two months later | Four months later | Immediately after preparation | Two months later | Four months later | Immediately after preparation | Two months later | Four months later | Immediately after preparation | Two months later | Four months later | Immediately after preparation | Four months later |
| Comparative Example 46 | 5 | 4 | 3 | 5 | 4 | 3 | 5 | 4 | 3 | 5 | 4 | 4 | Good | Good |
| Comparative Example 47 | 5 | 4 | 3 | 5 | 4 | 3 | 5 | 3 | 2 | 5 | 4 | 4 | Good | Good |
| Comparative Example 48 | 5 | 4 | 3 | 5 | 4 | 3 | 5 | 3 | 2 | 5 | 4 | 4 | Good | Good |
| Example 45 | 5 | 4 | 3 | 5 | 3 | 1 | 5 | 4 | 2 | 5 | 4 | 3 | Good | Good |
| Example 46 | 5 | 4 | 3 | 5 | 3 | 1 | 5 | 4 | 2 | 5 | 4 | 3 | Good | Good |
| Example 47 | 5 | 4 | 3 | 5 | 3 | 1 | 5 | 4 | 2 | 5 | 4 | 3 | Good | Good |
| Example 48 | 5 | 4 | 3 | 5 | 3 | 1 | 5 | 4 | 2 | 5 | 4 | 3 | Good | Good |

<Study on Compounding Ratio of Additives>

EXAMPLES 49 to 54

Solutions were prepared in accordance with the formulations shown in Table 17 in the same manner as in Example 1, and lyophilized to prepare dried influenza vaccine preparations. The obtained dried influenza vaccine preparations were stored at 40° C.±2° C. for four months, and the activity of the influenza HA antigen after the storage was measured by the SRID method. The dried influenza vaccine preparations were evaluated in accordance with the characteristic evaluation method. The results were scored, and Table 19 shows the scores.

EXAMPLES 55 to 60

Solutions were prepared in accordance with the formulations shown in Table 18 in the same manner as in Example 1, and lyophilized to prepare dried influenza vaccine preparations. The obtained dried influenza vaccine preparations were stored at 40° C.±2° C. for four months, and the activity of the influenza HA antigen after the storage was measured by the SRID method. The dried influenza vaccine preparations were evaluated in accordance with the characteristic evaluation method. The results were scored, and Table 20 shows the scores.

TABLE 17

| | Formulation [% by mass] Example | | | | | |
|---|---|---|---|---|---|---|
| Component | 49 | 50 | 51 | 52 | 53 | 54 |
| Tetravalent vaccine solution A | 50 | 50 | 50 | 50 | 50 | 50 |
| Dextran | 5 | 5 | 5 | 5 | 10 | 20 |
| Trehalose | 1 | 9 | 10 | 5 | 2 | 4 |

TABLE 17-continued

| Component | Formulation [% by mass] Example 49 | 50 | 51 | 52 | 53 | 54 |
|---|---|---|---|---|---|---|
| Arginine hydrochloride | 0.1 | 1 | 1 | 2 | 0.2 | 0.4 |
| Purified water | 43.9 | 35.0 | 34.0 | 38.0 | 37.8 | 25.6 |

TABLE 18

| Component | Formulation [% by mass] Example 55 | 56 | 57 | 58 | 59 | 60 |
|---|---|---|---|---|---|---|
| Tetravalent vaccine solution B | 50 | 50 | 50 | 50 | 50 | 50 |
| Dextran | 5 | 5 | 5 | 5 | 10 | 20 |
| Trehalose | 1 | 9 | 10 | 5 | 2 | 4 |
| Arginine hydrochloride | 0.1 | 1 | 1 | 2 | 0.2 | 0.4 |
| Purified water | 43.9 | 35.0 | 34.0 | 38.0 | 37.8 | 25.6 |

TABLE 19

| Antigen: [2012-13 strain] | Solid content [% by mass] Dextran | Trehalose | Arginine hydrochloride | Activity of influenza HA antigen H1N1/C Immediately after preparation | Two months later | Four months later | H3N2/V Immediately after preparation | Two months later | Four months later |
|---|---|---|---|---|---|---|---|---|---|
| Example 49 | 74.3 | 14.9 | 1.5 | 5 | 5 | 5 | 5 | 5 | 5 |
| Example 50 | 32.0 | 57.6 | 6.4 | 5 | 5 | 5 | 5 | 5 | 5 |
| Example 51 | 30.1 | 60.1 | 6.0 | 5 | 5 | 5 | 5 | 5 | 5 |
| Example 52 | 39.6 | 39.6 | 15.8 | 5 | 5 | 5 | 5 | 5 | 5 |
| Example 53 | 78.0 | 15.6 | 1.6 | 5 | 5 | 5 | 5 | 5 | 5 |
| Example 54 | 79.9 | 16.0 | 1.6 | 5 | 5 | 5 | 5 | 5 | 5 |

| Antigen: [2012-13 strain] | Activity of influenza HA antigen B/W Immediately after preparation | Two months later | Four months later | B/B Immediately after preparation | Two months later | Four months later | Characteristics Immediately after preparation | Four months later |
|---|---|---|---|---|---|---|---|---|
| Example 49 | 5 | 5 | 5 | 5 | 5 | 5 | Good | Good |
| Example 50 | 5 | 5 | 5 | 5 | 5 | 5 | Good | Good |
| Example 51 | 5 | 5 | 5 | 5 | 5 | 5 | Good | Good |
| Example 52 | 5 | 5 | 5 | 5 | 5 | 5 | Good | Good |
| Example 53 | 5 | 5 | 5 | 5 | 5 | 5 | Good | Good |
| Example 54 | 5 | 5 | 5 | 5 | 5 | 5 | Good | Good |

TABLE 20

| Antigen: [2013-14 strain] | Solid content [% by mass] Dextran | Trehalose | Arginine hydrochloride | Activity of influenza HA antigen H1N1/C Immediately after preparation | Two months later | Four months later | H3N2/T Immediately after preparation | Two months later | Four months later |
|---|---|---|---|---|---|---|---|---|---|
| Example 55 | 74.3 | 14.9 | 1.5 | 5 | 5 | 5 | 5 | 5 | 5 |
| Example 56 | 32.0 | 57.6 | 6.4 | 5 | 5 | 5 | 5 | 5 | 5 |
| Example 57 | 30.1 | 60.1 | 6.0 | 5 | 5 | 5 | 5 | 5 | 5 |
| Example 58 | 39.6 | 39.6 | 15.8 | 5 | 5 | 5 | 5 | 5 | 5 |
| Example 59 | 78.0 | 15.6 | 1.6 | 5 | 5 | 5 | 5 | 5 | 5 |
| Example 60 | 79.9 | 16.0 | 1.6 | 5 | 5 | 5 | 5 | 5 | 5 |

| Antigen: [2013-14 strain] | Activity of influenza HA antigen B/M Immediately after preparation | Two months later | Four months later | B/B Immediately after preparation | Two months later | Four months later | Characteristics Immediately after preparation | Four months later |
|---|---|---|---|---|---|---|---|---|
| Example 55 | 5 | 5 | 5 | 5 | 5 | 5 | Good | Good |
| Example 56 | 5 | 5 | 5 | 5 | 5 | 5 | Good | Good |
| Example 57 | 5 | 5 | 5 | 5 | 5 | 5 | Good | Good |

TABLE 20-continued

| | | | | | | | | |
|---|---|---|---|---|---|---|---|---|
| Example 58 | 5 | 5 | 5 | 5 | 5 | 5 | Good | Good |
| Example 59 | 5 | 5 | 5 | 5 | 5 | 5 | Good | Good |
| Example 60 | 5 | 5 | 5 | 5 | 5 | 5 | Good | Good |

As shown in Tables 19 and 20, in the case where the amount of dextran as an excipient was 5 to 20% by mass in the preparation solution, the moldability of the dried influenza vaccine preparation obtained after lyophilization was favorable and the stability of the activity of the influenza HA antigen was also favorable. When the compounding ratio of the disaccharide and the amino acid as the stabilizers to dextran that was a main base material was 20% or more and 2% or more, respectively, the stability of the activity of the influenza virus antigen was favorable.

The dried influenza vaccine preparations according to Examples 49 to 60 were all low-moisture-content dried preparations having a moisture content measured by the loss on drying test of 10% by mass or less.

<Evaluation of Stability and Immunity Induction of Adjuvant-Added Lyophilized Tetravalent HA Vaccine Preparation>

EXAMPLE 61

An amount of 10% by mass of dextran, 5% by mass of trehalose, 1% by mass of arginine hydrochloride, and 0.06% by mass of ND002 (Nitto Denko Corporation) that is a *Pantoea* agglomerance-derived LPS as an adjuvant were added to 33.94% by mass of purified water, and appropriately stirred to be dissolved. An amount of 50% by mass of the obtained solution was added to the tetravalent vaccine solution A, and mixed well. The obtained vaccine-containing preparation solution was dispensed in 0.25-g portions in aluminum packaging materials, and lyophilized to prepare a dried influenza vaccine preparation. The obtained dried influenza vaccine preparation was stored at 40° C.±2° C. for four months, and the activity of the influenza HA antigen after the storage was measured by the SRID method. The dried influenza vaccine preparation was evaluated in accordance with the characteristic evaluation method. The results were scored, and Table 23 shows the scores.

Figure 2:
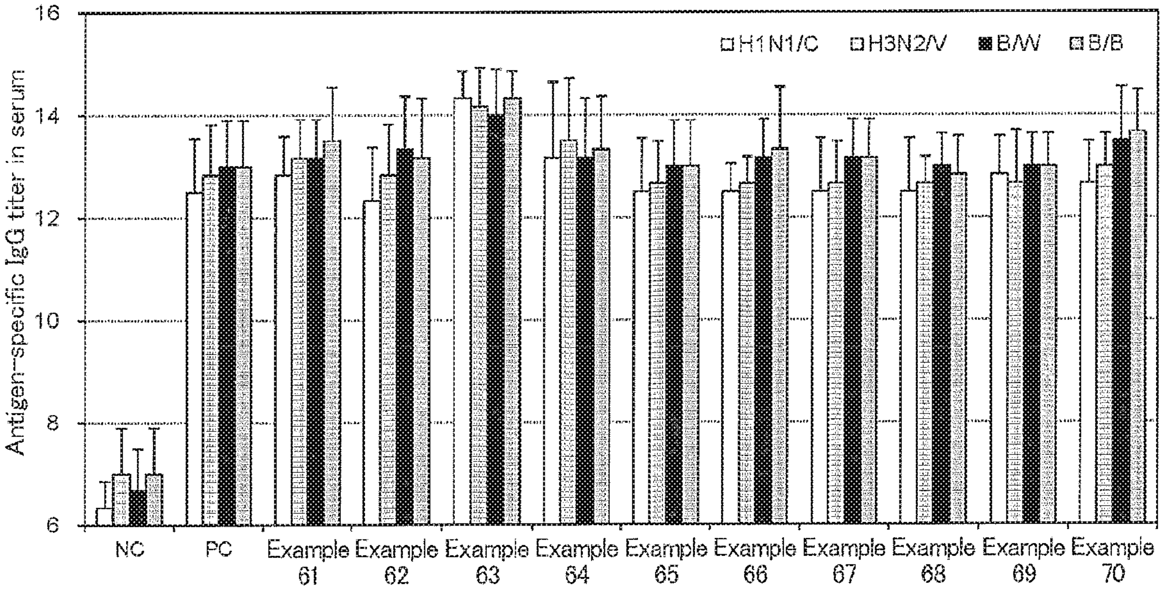
FIG. 2 is a graph showing the measurement results of the antigen-specific IgG titers of the dried influenza vaccine preparations according to Examples 61 to 70 in mouse serums.

In addition, an immunity induction test using a model animal for immunological evaluation was performed by the method described below, and FIGS. 1 and 2 show the results.

Mouse Immunity Test by Oral Administration

An immunity induction test using the dried influenza vaccine preparation prepared as described above was performed on a mouse as a model animal. First, the dried influenza vaccine preparation was dissolved in 3 mL of purified water to prepare a vaccine preparation solution (influenza HA antigen concentration: 5 μg/mL for each antigen). Next, a preliminarily prepared mouse (BALB/c mouse, 7-week-old female) was anesthetized, and 20 μL of the obtained vaccine preparation solution was administered to the mouse sublingually. A solution in which the concentrations of the influenza HA antigen and the adjuvant ND002 were the same as those of the vaccine preparation solution was prepared as a positive comparative example (PC). Also, a solution in which the concentration of the influenza HA antigen was the same as that of the vaccine preparation solution was prepared as a negative comparative example (NC). The prepared solutions were each similarly administered to a mouse.

One week after the administration, the mice were again anesthetized and the solutions were similarly administered thereto. One week after the second administration, the serums and nasal cavity washing liquids of the mice were collected. The blood was centrifuged at 3,000 G at 4° C. for 10 minutes. To 20 μL of the supernatant was added 300 μL of a phosphate buffer (Nacalai Tesque), thereby preparing a serum sample. The nasal cavity washing liquid was prepared by cutting a lower portion of the respiratory tract of the mouse, pouring 200 μL of a phosphate buffer (Nacalai Tesque) thereinto, and collecting the liquid reaching the nasal cavity, thereby preparing a nasal cavity washing liquid sample.

The systemic immune response was evaluated by measuring the antigen-specific IgG antibody in the mouse serum. In addition, the mucosal immune response was evaluated by measuring the antigen-specific IgA titer in the mouse nasal cavity washing liquid.

Method for Measuring Antigen-Specific IgG Titer in Mouse Serum (ELISA Method)

The influenza HA antigen-containing solutions (1.0 μg/mL) diluted with a carbonate buffer were each individually applied to a 96-well plate for ELISA in an amount of 100-μL portion, and left over night.

Next, a washing liquid was prepared. Specifically, an amount of 9.6 g of phosphate buffered saline powder (available from Nissui Pharmaceutical Co., Ltd., product name: Dulbecco PBS(-) "Nissui") and 0.5 mL of polyoxyethylene (20) monolaurate (Wako Pure Chemical Industries, Ltd.) were added per 1 of distilled water, and stirred to be sufficiently dissolved. The well-plate was washed with this washing liquid three times, and a blocking solution obtained by diluting a blocking agent (Block Ace available from Sumitomo Dainippon Pharma Co., Ltd.) with purified water to a concentration of 4 g/100 mL was added in an amount of 200 μL to the well plate. The well plate was allowed to stand at room temperature for two hours. Then, the well plate was washed with the washing liquid three times.

A serum preliminarily collected from a mouse was centrifuged at 3000 G at 4° C. for 10 minutes, and the supernatant was collected. Using a solution obtained by diluting the blocking agent with a phosphate buffer (Nacalai Tesque) to a concentration of 0.4 g/100 mL, the supernatant or nasal cavity washing liquid was serially diluted in two-fold increments, and each solution was added to the well plate in an amount of 50 μL. The well plate was allowed to stand at room temperature for two hours.

Then, the well plate was washed with the washing liquid three times. A HRP-labeled anti-mouse IgG antibody (Goat-anti mouse IgG Fc HRP, available from Bethyl Laboratories, Inc) was diluted 10,000 times with a solution obtained by diluting a blocking agent with a phosphate buffer (Nacalai Tesque) to a concentration of 0.4 g/100 mL, and the obtained solution was added to the well plate in an amount of 100 μL. The well plate was allowed to stand at room temperature for one hour.

Then, the well plate was washed with the washing liquid three times, and a TMB solution (ELISA POD TMB kit, available from Nacalai Tesque) was added to the well plate in an amount of 100 μL. The well plate was allowed to stand in a dark place for 30 minutes.

Then, 1M sulfuric acid solution was added to the well plate in an amount of 100 μL, and using the resulting 96-well plate, the absorbance at 450 nm was measured with a microplate reader (SpectraMax M2[e], available from Molecular Devices). Based on the absorbance of serially diluted solutions, the IgG antibody titer in the mouse serum was obtained using Log 2.

Method for Measuring Antigen-Specific IgA Titer in Mouse Nasal Cavity Washing Liquid (ELISA Method)

Operations were carried out basically in the same manner as in the method for measuring the antigen-specific IgG titer, except that the measurement sample was a nasal cavity washing liquid and HRP-labeled mouse IgA antibody (Goat-anti-mouse IgA α HRP, available from Bethyl Laboratories, Inc.) was used instead of the HRP-labeled antimouse IgG antibody.

EXAMPLES 62 to 70

Solutions were prepared in accordance with the formulations shown in Table 21 in the same manner as in Example 61, and lyophilized to prepare dried influenza vaccine preparations. The obtained dried influenza vaccine preparations were stored at 40° C.±2° C. for four months, and the activity of the influenza HA antigen after the storage was measured by the SRTD method. The dried influenza vaccine preparations were evaluated in accordance with the characteristic evaluation method. The results were scored, and Table 23 shows the scores.

In addition, an immunity induction test was performed on a model animal for immunological evaluation by the ELISA method, and FIGS. 1 and 2 show the results.

EXAMPLES 71 to 80

In the same manner as in Example 61, solutions were prepared in accordance with the formulations shown in Table 22, and lyophilized to prepare dried influenza vaccine preparations. The tetravalent vaccine solution used was type B. The obtained dried influenza vaccine preparations were stored at 40° C.±2° C. for four months, and the activity of the vaccine after the storage was measured by the SRID method. The dried influenza vaccine preparations were evaluated in accordance with the characteristic evaluation method. The results were scored, and Table 24 shows the scores.

Figure 3:
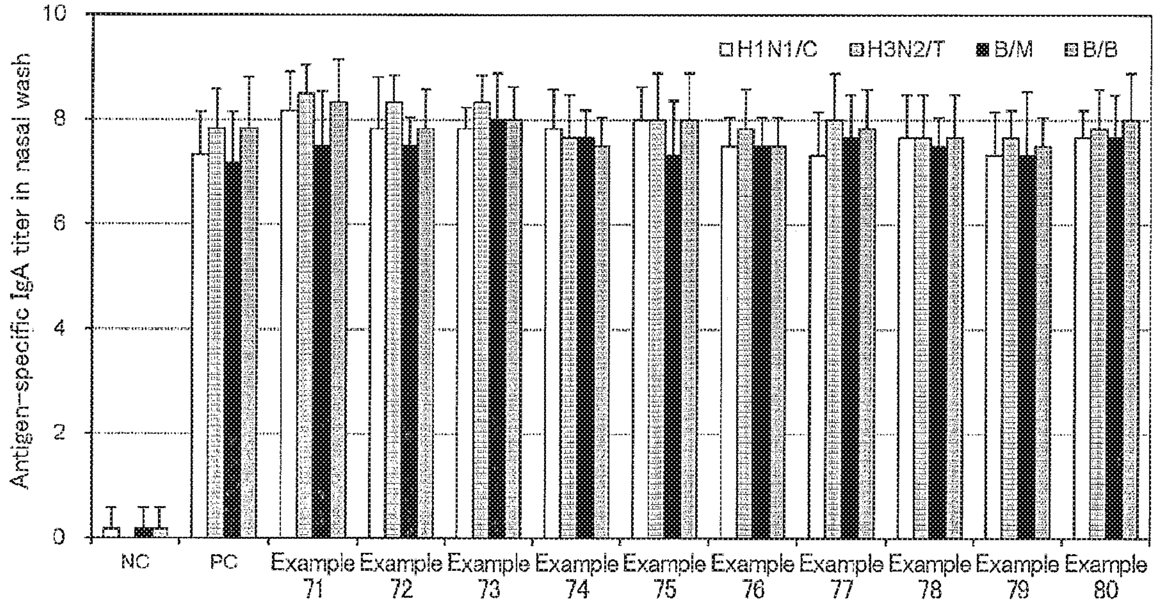
FIG. 3 is a graph showing the measurement results of the antigen-specific IgA titers of dried influenza vaccine preparations according to Examples 71 to 80 in mouse nasal cavity washing liquids.
Figure 4:
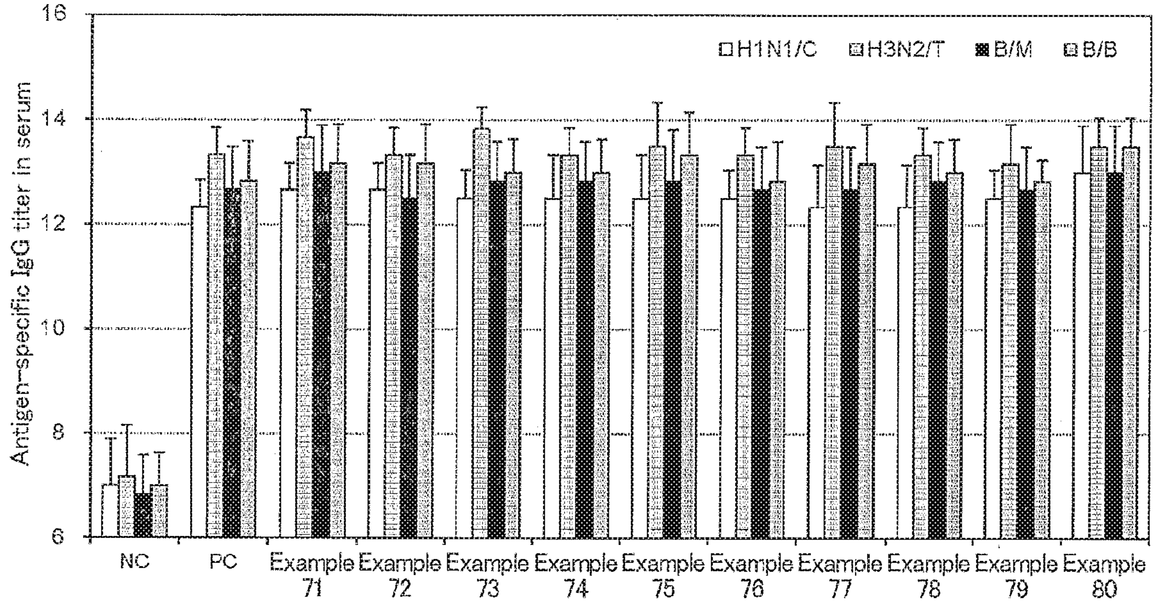
FIG. 4 is a graph showing the measurement results of the antigen-specific IgG titers of the dried influenza vaccine preparations according to Examples 71 to 80 in mouse serums.

In addition, an immunity induction test was performed on a model animal for immunological evaluation by the ELISA method. FIGS. 3 and 4 show the results.

TABLE 21

| | Formulation [% by mass] Example | | | | | | | | | |
|---|---|---|---|---|---|---|---|---|---|---|
| Component | 61 | 62 | 63 | 64 | 65 | 66 | 67 | 68 | 69 | 70 |
| Tetravalent vaccine solution A | 50 | 50 | 50 | 50 | 50 | 50 | 50 | 50 | 50 | 50 |
| Dextran | 10 | 10 | 10 | 10 | 10 | 10 | 10 | 10 | 10 | 10 |
| ND002 | 0.06 | 0.06 | 0.06 | 0.06 | 0.06 | 0.06 | 0.06 | 0.06 | 0.006 | 0.6 |
| Trehalose | 5 | 5 | 5 | 5 | — | — | — | — | 5 | 5 |
| Isomalt | — | — | — | — | 5 | 5 | 5 | 5 | — | — |
| Arginine hydrochloride | 1 | — | — | — | 1 | — | — | — | 1 | 1 |
| Proline | — | 1 | — | — | — | 1 | — | — | — | — |
| Threonine | — | — | 1 | — | — | — | 1 | — | — | — |
| Lysine hydrochloride | — | — | — | 1 | — | — | — | 1 | — | — |
| Purified water | 33.94 | 33.94 | 33.94 | 33.94 | 33.94 | 33.94 | 33.94 | 33.94 | 33.994 | 33.40 |

TABLE 22

| | Formulation [% by mass] Example | | | | | | | | | |
|---|---|---|---|---|---|---|---|---|---|---|
| Component | 71 | 72 | 73 | 74 | 75 | 76 | 77 | 78 | 79 | 80 |
| Tetravalent vaccine solution B | 50 | 50 | 50 | 50 | 50 | 50 | 50 | 50 | 50 | 50 |
| Dextran | 10 | 10 | 10 | 10 | 10 | 10 | 10 | 10 | 10 | 10 |
| ND002 | 0.06 | 0.06 | 0.06 | 0.06 | 0.06 | 0.06 | 0.06 | 0.06 | 0.006 | 0.6 |
| Trehalose | 5 | 5 | 5 | 5 | — | — | — | — | 5 | 5 |
| Isomalt | — | — | — | — | 5 | 5 | 5 | 5 | — | — |
| Arginine hydrochloride | 1 | — | — | — | 1 | — | — | — | 1 | 1 |
| Proline | — | 1 | — | — | — | 1 | — | — | — | — |
| Threonine | — | — | 1 | — | — | — | 1 | — | — | — |
| Lysine hydrochloride | — | — | — | 1 | — | — | — | 1 | — | — |
| Purified water | 33.94 | 33.94 | 33.94 | 33.94 | 33.94 | 33.94 | 33.94 | 33.94 | 33.994 | 33.40 |

TABLE 23

| Antigen: [2012-13 strain] | Activity of influenza HA antigen | | | | | | | | | | | |
|---|---|---|---|---|---|---|---|---|---|---|---|---|
| | H1N1/C | | | H3N2/V | | | B/W | | | B/B | | |
| | Immediately after preparation | Two months later | Four months later | Immediately after preparation | Two months later | Four months later | Immediately after preparation | Two months later | Four months later | Immediately after preparation | Two months later | Four months later |
| Example 61 | 5 | 5 | 5 | 5 | 5 | 5 | 5 | 5 | 5 | 5 | 5 | 5 |
| Example 62 | 5 | 5 | 5 | 5 | 5 | 5 | 5 | 5 | 5 | 5 | 5 | 5 |
| Example 63 | 5 | 5 | 5 | 5 | 5 | 5 | 5 | 5 | 5 | 5 | 5 | 5 |
| Example 64 | 5 | 5 | 5 | 5 | 5 | 5 | 5 | 5 | 5 | 5 | 5 | 5 |
| Example 65 | 5 | 5 | 5 | 5 | 5 | 5 | 5 | 5 | 5 | 5 | 5 | 5 |
| Example 66 | 5 | 5 | 5 | 5 | 5 | 5 | 5 | 5 | 5 | 5 | 5 | 5 |
| Example 67 | 5 | 5 | 5 | 5 | 5 | 5 | 5 | 5 | 5 | 5 | 5 | 5 |
| Example 68 | 5 | 5 | 5 | 5 | 5 | 5 | 5 | 5 | 5 | 5 | 5 | 5 |
| Example 69 | 5 | 5 | 5 | 5 | 5 | 5 | 5 | 5 | 5 | 5 | 5 | 5 |
| Example 70 | 5 | 5 | 5 | 5 | 5 | 5 | 5 | 5 | 5 | 5 | 5 | 5 |

TABLE 24

| Antigen: [2013-14 strain] | Activity of influenza HA antigen | | | | | | | | | | | |
|---|---|---|---|---|---|---|---|---|---|---|---|---|
| | H1N1/C | | | H3N2/T | | | B/M | | | B/B | | |
| | Immediately after preparation | Two months later | Four months later | Immediately after preparation | Two months later | Four months later | Immediately after preparation | Two months later | Four months later | Immediately after preparation | Two months later | Four months later |
| Example 71 | 5 | 5 | 5 | 5 | 5 | 5 | 5 | 5 | 5 | 5 | 5 | 5 |
| Example 72 | 5 | 5 | 5 | 5 | 5 | 5 | 5 | 5 | 5 | 5 | 5 | 5 |
| Example 73 | 5 | 5 | 5 | 5 | 5 | 5 | 5 | 5 | 5 | 5 | 5 | 5 |
| Example 74 | 5 | 5 | 5 | 5 | 5 | 5 | 5 | 5 | 5 | 5 | 5 | 5 |
| Example 75 | 5 | 5 | 5 | 5 | 5 | 5 | 5 | 5 | 5 | 5 | 5 | 5 |
| Example 76 | 5 | 5 | 5 | 5 | 5 | 5 | 5 | 5 | 5 | 5 | 5 | 5 |
| Example 77 | 5 | 5 | 5 | 5 | 5 | 5 | 5 | 5 | 5 | 5 | 5 | 5 |
| Example 78 | 5 | 5 | 5 | 5 | 5 | 5 | 5 | 5 | 5 | 5 | 5 | 5 |
| Example 79 | 5 | 5 | 5 | 5 | 5 | 5 | 5 | 5 | 5 | 5 | 5 | 5 |
| Example 80 | 5 | 5 | 5 | 5 | 5 | 5 | 5 | 5 | 5 | 5 | 5 | 5 |

As shown in Tables 23 and 24, in the dried influenza vaccine preparation of the present invention containing an excipient, a disaccharide, and an amino acid, the activities of all of the tetravalent influenza HA antigens could be stabilized even in the case where an adjuvant was contained.

The dried influenza vaccine preparations according to Examples 61 to 80 were all low-moisture-content dried preparations having a moisture content measured by a loss on drying test of 10% by mass or less.

Moreover, as shown in FIGS. 1 to 4, the dried influenza vaccine preparations according to Examples 61 to 80 could effectively induce systemic immune response and mucosa immune response even by oral administration.

<Study on Compounding Ratio of Additives in Production of Tablet>

EXAMPLES 81 to 116

Solutions were prepared in accordance with the formulations shown in Table 25 in the same manner as in Example 1, and lyophilized to prepare dried influenza vaccine preparations. The tactile feel and persistence of the obtained dried influenza vaccine preparations were sensory evaluated. Table 26 shows the results.

In Table 25, "HPC-SSL" refers to hydroxypropyl cellulose (available from Nippon Soda Co., Ltd., product name: Nisso HPC SSL), and "HPMC" refers to hydroxypropyl methylcellulose (available from Shin-Etsu Chemical Co., Ltd., product name: TC-5E).

The term "tactile feel" refers to a touch sensed when picking the influenza dried preparation with fingers, and "persistence" indicates the presence or absence of a solid component visually observed on a packaging material after the influenza dried preparation was taken out. When the tactile feel is rated as "hard", the influenza dried preparation has high physical strength and is favorable in terms of handleability as a dried vaccine preparation. The persistence rated as "absent" means that the solid component of the influenza dried preparation entirely maintains its form as a solid preparation, and no active ingredients are likely to be left on a packaging material. In relation to the amounts (% by mass) of the solid components in each table, the rest to reach 100% is the proportion of a solid component of the buffer and the like as described above.

TABLE 25

| Component | Example | | | | | | | | | | | |
|---|---|---|---|---|---|---|---|---|---|---|---|---|
| | 81 | 82 | 83 | 84 | 85 | 86 | 87 | 88 | 89 | 90 | 91 | 92 |
| Tetravalent vaccine solution A | 50 | 50 | 50 | 50 | 50 | 50 | 50 | 50 | 50 | 50 | 50 | 50 |
| Dextran | 2 | 2 | 2 | 4 | 4 | 4 | 5 | 5 | 5 | 7 | 7 | 7 |

TABLE 25-continued

| | | | | | | | | | | | | |
|---|---|---|---|---|---|---|---|---|---|---|---|---|
| Trehalose | 4 | 2.5 | 1 | 8 | 5 | 2 | 10 | 6.25 | 2.5 | 14 | 8.75 | 3.5 |
| Arginine hydrochloride | 0.5 | 0.5 | 0.2 | 1 | 1 | 0.4 | 1.25 | 1.25 | 0.5 | 1.75 | 1.75 | 0.7 |
| Purified water | 43.5 | 45.0 | 46.8 | 37.0 | 40.0 | 43.6 | 33.8 | 37.5 | 42.0 | 27.3 | 32.5 | 38.8 |

| | Example | | | | | | | | | | | |
|---|---|---|---|---|---|---|---|---|---|---|---|---|
| Component | 93 | 94 | 95 | 96 | 97 | 98 | 99 | 100 | 101 | 102 | 103 | 104 |
| Tetravalent vaccine solution A | 50 | 50 | 50 | 50 | 50 | 50 | 50 | 50 | 50 | 50 | 50 | 50 |
| HPC-SSL | 2 | 2 | 2 | 4 | 4 | 4 | 5 | 5 | 5 | 7 | 7 | 7 |
| Trehalose | 4 | 2.5 | 1 | 8 | 5 | 2 | 10 | 6.25 | 2.5 | 14 | 8.75 | 3.5 |
| Arginine hydrochloride | 0.5 | 0.5 | 0.2 | 1 | 1 | 0.4 | 1.25 | 1.25 | 0.5 | 1.75 | 1.75 | 0.7 |
| Purified water | 43.5 | 45.0 | 46.8 | 37.0 | 40.0 | 43.6 | 33.8 | 37.5 | 42.0 | 27.3 | 32.5 | 38.8 |

| | Example | | | | | | | | | | | |
|---|---|---|---|---|---|---|---|---|---|---|---|---|
| Component | 105 | 106 | 107 | 108 | 109 | 110 | 111 | 112 | 113 | 114 | 115 | 116 |
| Tetravalent vaccine solution A | 50 | 50 | 50 | 50 | 50 | 50 | 50 | 50 | 50 | 50 | 50 | 50 |
| HPMC | 2 | 2 | 2 | 4 | 4 | 4 | 5 | 5 | 5 | 7 | 7 | 7 |
| Trehalose | 4 | 2.5 | 1 | 8 | 5 | 2 | 10 | 6.25 | 2.5 | 14 | 8.75 | 3.5 |
| Arginine hydrochloride | 0.5 | 0.5 | 0.2 | 1 | 1 | 0.4 | 1.25 | 1.25 | 0.5 | 1.75 | 1.75 | 0.7 |
| Purified water | 43.5 | 45.0 | 46.8 | 37.0 | 40.0 | 43.6 | 33.8 | 37.5 | 42.0 | 27.3 | 32.5 | 38.8 |

TABLE 26

| | Solid content [% by mass] | | | Physical properties | |
|---|---|---|---|---|---|
| Antigen: [2012-13 strain] | Dextran | Trehalose | Arginine hydrochloride | Tactile feel | Persistence |
| Example 81 | 28.1 | 56.1 | 7.0 | Very soft | Present |
| Example 82 | 35.5 | 44.4 | 8.9 | Very soft | Slightly present |
| Example 83 | 52.2 | 26.1 | 5.2 | Very soft | Absent |
| Example 84 | 29.4 | 58.7 | 7.3 | Soft | Present |
| Example 85 | 37.6 | 47.0 | 9.4 | Soft | Slightly present |
| Example 86 | 56.9 | 28.5 | 5.7 | Soft | Absent |
| Example 87 | 29.6 | 59.2 | 7.4 | Hard | Present |
| Example 88 | 38.1 | 47.6 | 9.5 | Hard | Slightly present |
| Example 89 | 57.9 | 29.0 | 5.8 | Hard | Absent |
| Example 90 | 29.9 | 59.9 | 7.5 | Hard | Present |
| Example 91 | 38.6 | 48.3 | 9.7 | Hard | Slightly present |
| Example 92 | 59.2 | 29.6 | 5.9 | Hard | Absent |

| | Solid content [% by mass] | | | Physical properties | |
|---|---|---|---|---|---|
| Antigen: [2012-13 strain] | HPC-SSL | Trehalose | Arginine hydrochloride | Tactile feel | Persistence |
| Example 93 | 28.1 | 56.1 | 7.0 | Very soft | Present |
| Example 94 | 35.5 | 44.4 | 8.9 | Very soft | Slightly present |
| Example 95 | 52.2 | 26.1 | 6.2 | Very soft | Absent |
| Example 96 | 29.4 | 58.7 | 7.3 | Soft | Present |
| Example 97 | 37.6 | 47.0 | 9.4 | Soft | Slightly present |
| Example 98 | 56.9 | 28.5 | 5.7 | Soft | Absent |
| Example 99 | 29.6 | 59.2 | 7.4 | Hard | Present |
| Example 100 | 38.1 | 47.6 | 9.5 | Hard | Slightly present |
| Example 101 | 57.9 | 29.0 | 5.8 | Hard | Absent |
| Example 102 | 29.9 | 59.9 | 7.5 | Hard | Present |
| Example 103 | 38.6 | 48.3 | 9.7 | Hard | Slightly present |
| Example 104 | 59.2 | 29.6 | 5.9 | Hard | Absent |

| | Solid content [% by mass] | | | Physical properties | |
|---|---|---|---|---|---|
| Antigen: [2012-13 strain] | HPMC | Trehalose | Arginine hydrochloride | Tactile feel | Persistence |
| Example 105 | 28.1 | 56.1 | 7.0 | Very soft | Present |
| Example 106 | 35.5 | 44.4 | 8.9 | Very soft | Slightly present |
| Example 107 | 52.2 | 26.1 | 5.2 | Very soft | Absent |
| Example 108 | 29.4 | 58.7 | 7.3 | Soft | Present |
| Example 109 | 37.6 | 47.0 | 9.4 | Soft | Slightly present |

TABLE 26-continued

| | | | | | |
|---|---|---|---|---|---|
| Example 110 | 56.9 | 28.5 | 5.7 | Soft | Absent |
| Example 111 | 29.6 | 59.2 | 7.4 | Hard | Present |
| Example 112 | 38.1 | 47.6 | 9.5 | Hard | Slightly present |
| Example 113 | 57.9 | 29.0 | 5.8 | Hard | Absent |
| Example 114 | 29.9 | 59.9 | 7.5 | Hard | Present |
| Example 115 | 38.6 | 48.3 | 9.7 | Hard | Slightly present |
| Example 116 | 59.2 | 29.6 | 5.9 | Hard | Absent |

As shown in Tables 25 and 26, in Examples 81 to 86, 93 to 98, and 105 to 110 in which the amount of the excipient was 2% by mass or 4% by mass in the state of a solution before lyophilization (vaccine-containing preparation aqueous solution), the tactile feel of the dried preparation was "soft" or "very soft", while in Examples 87 to 92, 99 to 104, and 111 to 116 in which the amount of the excipient was 5% by mass or 7% by mass in the state of a solution (vaccine-containing preparation aqueous solution) the tactile feel of the dried preparation was "hard". In Examples 83, 86, 89, 92, 95, 98, 101, 104, 107, 110, 113, and 116 in which the amount of the excipient in the lyophilized preparation was more than 30% by mass, no adhesion of a solid component was observed, while in Examples 81, 82, 84, 85, 87, 88, 90, 91, 93, 94, 96, 97, 99, 100, 102, 103, 105, 106, 108, 109, 111, 112 114, and 115 in which the formulation of the lyophilized preparation was not within the above range, adhesion of a solid component was observed.

INDUSTRIAL APPLICABILITY

The present invention can provide a vaccine pharmaceutical composition for oral administration in which an influenza virus antigen can exhibit high activity without a decrease in the activity even during the production process of the dried preparation and can stably maintain the activity even when the pharmaceutical composition is stored without strictly maintaining a low temperature. The present invention also can provide a method for producing the pharmaceutical composition.

The invention claimed is:

1. A vaccine pharmaceutical composition for oral administration comprising:

an influenza virus antigen;

an excipient comprising at least one selected from the group consisting of dextran, hydroxypropyl cellulose, and hydroxypropyl methylcellulose;

a disaccharide; and an amino acid selected from the group consisting of arginine, lysine, proline, threonine, ornithine, glycine, and salts of these;

wherein:

a total amount of the excipient is 30 to 95% by mass relative to the mass of the solid content of the vaccine pharmaceutical composition; and the vaccine pharmaceutical composition is a dried preparation.

2. The vaccine pharmaceutical composition for oral administration according to claim 1, wherein the disaccharide is at least one selected from the group consisting of trehalose, isomalt, sucrose, maltose, melibiose, palatinose, and lactulose.

3. The vaccine pharmaceutical composition for oral administration according to claim 1, wherein the dried preparation is a tablet.

4. The vaccine pharmaceutical composition for oral administration according to claim 1, wherein the excipient contains dextran.

5. The vaccine pharmaceutical composition for oral administration according to claim 4, wherein the amount of the dextran is 30 to 95% by mass relative to the solid content of the vaccine pharmaceutical composition for oral administration.

6. The vaccine pharmaceutical composition for oral administration according to claim 1, wherein the amino acid is selected from the group consisting of arginine and a salt thereof.

7. The vaccine pharmaceutical composition for oral administration according to claim 6, wherein the amount of the at least one selected from the group consisting of arginine and a salt thereof is 1 to 19% by mass relative to the solid content of the vaccine pharmaceutical composition for oral administration.

8. The vaccine pharmaceutical composition for oral administration according to claim 1, wherein the salt of the amino acid is an inorganic salt.

9. The vaccine pharmaceutical composition for oral administration according to claim 8, wherein the inorganic salt is hydrochloride.

10. The vaccine pharmaceutical composition for oral administration according to claim 1, wherein the influenza virus antigen is an inactivated antigen.

11. The vaccine pharmaceutical composition for oral administration according to claim 10, wherein the inactivated antigen is a split vaccine antigen or a subunit vaccine antigen.

12. The vaccine pharmaceutical composition for oral administration according to claim 1, wherein the influenza virus antigen is a multivalent antigen containing plural antigens.

13. A method for producing a vaccine pharmaceutical composition for oral administration, comprising:

preparing a vaccine-containing preparation solution that contains an influenza virus antigen, an excipient, a disaccharide, an amino acid, and a solvent; and drying the vaccine-containing preparation solution.

14. A method for producing a vaccine pharmaceutical composition for oral administration, comprising:

preparing a vaccine-containing preparation solution that contains an influenza virus antigen, an excipient, a disaccharide, an amino acid, and a solvent; and drying the vaccine-containing preparation solution, wherein the vaccine-containing preparation solution is dried by lyophilization, and the vaccine-containing preparation solution contains 5% by mass or more of the excipient relative to the mass of the vaccine-containing preparation solution and 30% by mass or more of the excipient relative to the mass of the solid content of the vaccine-containing preparation solution.

15. The vaccine pharmaceutical composition for oral administration according to claim 1, wherein a total amount of the disaccharide is 10 to 70% by mass relative to the mass of the solid content of the vaccine pharmaceutical composition for oral administration.

16. The vaccine pharmaceutical composition for oral administration according to claim 1, wherein an amount of the amino acid is 1 to 19% by mass relative to the mass of the solid content of the vaccine pharmaceutical composition for oral administration.

* * * * *